(12) United States Patent
Forman et al.

(10) Patent No.: US 10,064,630 B2
(45) Date of Patent: Sep. 4, 2018

(54) DRIVER ASSEMBLIES, DRIVERS, INTRAOSSEOUS DEVICES, AND METHODS FOR DETERMINING VOLTAGES AND/OR IMPEDANCES IN BIOLOGICAL MATERIAL

(71) Applicant: TELEFLEX MEDICAL DEVICES S.À R.L., Luxembourg (LU)

(72) Inventors: Michael Robert Forman, Los Gatos, CA (US); Eric Norman Rudie, Maple Grove, MN (US)

(73) Assignee: TELEFLEX MEDICAL DEVICES S.À R.L., Luxembourg (LU)

( * ) Notice: Subject to any disclaimer, the term of this patent is extended or adjusted under 35 U.S.C. 154(b) by 554 days.

(21) Appl. No.: 13/836,548

(22) Filed: Mar. 15, 2013

(65) Prior Publication Data

US 2014/0276839 A1    Sep. 18, 2014

(51) Int. Cl.
| | |
|---|---|
| A61B 17/16 | (2006.01) |
| A61B 10/02 | (2006.01) |
| A61B 50/33 | (2016.01) |
| A61B 46/10 | (2016.01) |
| A61B 90/00 | (2016.01) |
| A61B 17/00 | (2006.01) |
| A61B 50/30 | (2016.01) |

(52) U.S. Cl.
CPC ........ *A61B 17/1624* (2013.01); *A61B 10/025* (2013.01); *A61B 17/1615* (2013.01); *A61B 17/1622* (2013.01); *A61B 17/1626* (2013.01); *A61B 46/10* (2016.02); *A61B 50/33* (2016.02); *A61B 17/162* (2013.01); *A61B 2010/0258* (2013.01); *A61B 2017/0003* (2013.01); *A61B 2017/00473* (2013.01); *A61B 2017/00477* (2013.01); *A61B 2050/3008* (2016.02); *A61B 2090/062* (2016.02)

(58) Field of Classification Search
None
See application file for complete search history.

(56) References Cited

U.S. PATENT DOCUMENTS

| | | | | | |
|---|---|---|---|---|---|
| 4,399,813 | A | * | 8/1983 | Barber | A61B 17/1615 606/100 |
| 4,927,403 | A | * | 5/1990 | Pate, Sr. | E21B 17/028 174/138 D |
| 5,514,150 | A | * | 5/1996 | Rostoker | A61B 17/00234 604/22 |
| 5,902,105 | A | * | 5/1999 | Uejima | A61C 19/041 433/27 |

(Continued)

FOREIGN PATENT DOCUMENTS

| | | |
|---|---|---|
| EP | 1384436 A2 | 1/2004 |
| WO | 2004066850 A1 | 8/2004 |

OTHER PUBLICATIONS

International Search Report and Written Opinion issued in PCT/US2014/029356, dated Aug. 21, 2014.

(Continued)

*Primary Examiner* — Hemant M Desai
*Assistant Examiner* — Mobeen Ahmed
(74) *Attorney, Agent, or Firm* — Baker & Hostetler LLP

(57) ABSTRACT

Driver assemblies, drivers, drill bits, and methods for determining information (such as impedances, voltages, voltage differences, and changes in such information) about biological material during a medical procedure.

20 Claims, 16 Drawing Sheets

(56) References Cited

U.S. PATENT DOCUMENTS

| | | | |
|---|---|---|---|
| 5,941,876 A * | 8/1999 | Nardella | A61B 17/32002 604/22 |
| 6,227,549 B1 * | 5/2001 | Michel | B23B 31/1215 269/274 |
| 6,391,005 B1 * | 5/2002 | Lum | A61B 5/053 600/506 |
| 6,665,948 B1 * | 12/2003 | Kozin | A61B 17/1626 175/45 |
| 6,863,136 B2 * | 3/2005 | Bar-Cohen | E21B 7/24 175/20 |
| 8,142,365 B2 * | 3/2012 | Miller | A61B 10/025 600/566 |
| 8,998,985 B2 * | 4/2015 | Gross | A61F 11/00 606/108 |
| 2001/0014439 A1 * | 8/2001 | Meller | A61C 1/081 433/50 |
| 2003/0004431 A1 * | 1/2003 | Pinyayev | A61B 5/0531 600/547 |
| 2003/0187366 A1 * | 10/2003 | Hashimshony | A61B 5/0507 600/547 |
| 2004/0267257 A1 * | 12/2004 | Bourne | A61B 18/1487 606/41 |
| 2005/0119660 A1 * | 6/2005 | Bourlion | A61B 5/053 606/80 |
| 2005/0165328 A1 | 7/2005 | Heske et al. | 600/566 |
| 2006/0173374 A1 * | 8/2006 | Neubardt | A61B 17/7092 600/547 |
| 2006/0178593 A1 * | 8/2006 | Neubardt | A61B 17/1626 600/547 |
| 2006/0206132 A1 | 9/2006 | Conquergood et al. | 606/180 |
| 2006/0241628 A1 * | 10/2006 | Parak | A61B 17/1626 606/80 |
| 2007/0100336 A1 * | 5/2007 | McFarlin | A61B 5/04001 606/45 |
| 2007/0191915 A1 * | 8/2007 | Strother | A61B 17/1626 607/63 |
| 2008/0045965 A1 * | 2/2008 | Miller | A61B 10/025 606/80 |
| 2008/0086140 A1 * | 4/2008 | Wolf | A61B 5/0488 606/79 |
| 2008/0167659 A1 * | 7/2008 | Bourlion | A61B 5/053 606/102 |
| 2008/0228072 A1 * | 9/2008 | Nycz | A61B 5/05 600/437 |
| 2008/0262526 A1 * | 10/2008 | Neubardt | A61B 17/1615 606/180 |
| 2008/0275378 A1 * | 11/2008 | Herndon | A61B 5/15134 604/22 |
| 2009/0069716 A1 | 3/2009 | Freeman et al. | 600/583 |
| 2009/0245956 A1 | 10/2009 | Apkarian et al. | |
| 2010/0145373 A1 * | 6/2010 | Alon | A61B 17/1662 606/169 |
| 2010/0331883 A1 * | 12/2010 | Schmitz | A61B 10/0275 606/249 |
| 2011/0046507 A1 | 2/2011 | Herndon | 600/547 |
| 2011/0046626 A1 * | 2/2011 | Herndon | A61B 5/053 606/80 |
| 2013/0060278 A1 * | 3/2013 | Bozung | A61B 34/20 606/205 |
| 2013/0149660 A1 * | 6/2013 | Pruckner | A61B 17/16 433/27 |
| 2013/0178858 A1 * | 7/2013 | Ye | A61B 17/162 606/80 |
| 2014/0073985 A1 * | 3/2014 | Sakai | A61B 5/4887 600/554 |

OTHER PUBLICATIONS

Tong In Oh et al., "Flexible electrode belt for EIT using nanofiber web dry electrodes," Institute of Physics and Engineering in Medicine, vol. 33, No. 10, 2012.

European Patent Office, Extended European Search Report for EP Patent Application No. 14763900.9, dated Nov. 2, 2016.

Canadian Intellectual Property Office, Communication regarding Canadian Patent Application No. 2907252, dated Dec. 22, 2016.

* cited by examiner

DRIVER ASSEMBLIES, DRIVERS, INTRAOSSEOUS DEVICES, AND METHODS FOR DETERMINING VOLTAGES AND/OR IMPEDANCES IN BIOLOGICAL MATERIAL

BACKGROUND

Field of the Invention

The present invention relates generally to driver assemblies, such as those including a driver (e.g., manual or powered) and a drill bit, to drivers, to drill bits, and to methods of determining information when penetrating biological material, and more particularly, but not by way of limitation, to driver assemblies that include drivers and drill bits that can be used to determine information (e.g., voltages, voltage differences, impedances, changes in voltage differences, changes in impedances, and the like) about a target area in biological material (e.g., such as bone (and, more specifically, an intraosseous space within bone) or cerebrospinal fluid), to drill bits usable with such drivers and driver assemblies, to such drivers, and to methods of determining information, like penetrator (e.g., drill bit) position within biological material and voltage differences and/or impedances related to a target area (or a change in voltage differences and/or impedances from a reference location, voltage difference, or impedance in a target area) within biological material.

SUMMARY

This disclosure includes embodiments of driver assemblies comprising a driver having at least one sensor and a penetrator that are configured to permit the driver assembly to determine information about a target area within biological material, such as bone or cerebrospinal fluid. For example, embodiments of the present driver assemblies can be configured to display information relating to the voltage and/or electrical impedance of biological material. As another example, embodiments of the present driver assemblies can be configured to display information relating to the position of a penetrator within biological material. This disclosure also includes embodiments of penetrators, such as drill bits, that may be coupled to drivers and used to assist in determining such information. This disclosure also includes embodiments of methods of determining information (e.g., electrical impedance, voltage, voltage differences, changes in impedances and/or voltage differences, and the like) concerning a target area within biological material. Embodiments of the present driver assemblies, drill bits, and methods may be useful in procedures such as those that establish access to an intraosseous (IO) space, bone marrow biopsies, and craniotomies, to name a few.

Some embodiments of the present driver assemblies comprise a driver comprising a controller; a motor coupled to a power source and further coupled to the controller such that the controller can affect the motor's operation; a drive shaft coupled to the motor such that the motor can move the drive shaft; a trigger coupled to the controller and configured to activate the motor; and a first electrode configured to be coupled to the controller; and a drill bit configured to be coupled to the drive shaft and the controller, the drill bit comprising: an outer surface; a core disposed inside the outer surface; and an insulator disposed between the core and the outer surface configured to prevent electrical communication between the core and the outer surface; where the outer surface, the insulator, and the core cooperate to form at least one tip of the drill bit; and where the controller is configured to determine at least one of a voltage difference between the core and the first electrode and an impedance when the first electrode is coupled to the controller and at least when the driver assembly is used in a medical procedure. In some embodiments, a portion of the core is exposed at the tip of the drill bit.

Some embodiments of the present driver assemblies comprise a two-wire configuration. In some embodiments, the impedance is a normalized impedance when the controller determines an impedance. In some embodiments, the drill bit is configured to be coupled to the drive shaft by a commutating electrical connection. In some embodiments, the drill bit is configured to be coupled to the drive shaft by a gear box bearing, the gear box bearing configured to permit a commutating electrical connection between the drill bit and the drive shaft. In some embodiments, the controller is configured to pass an alternating current to the core.

Some embodiments of the present driver assemblies comprise a second electrode configured to be coupled to the controller, the controller configured to pass a current to the second electrode, when the first and second electrodes are coupled to the controller, to permit the controller to determine at least one of a voltage difference between the core and the first electrode and an impedance at least when the driver assembly is used in a medical procedure. In some embodiments, at least one of the first electrode and the second electrode comprises an adhesive configured to adhere at least one of the first electrode and the second electrode to skin. In some embodiments, the assemblies comprise a patch connector configured to couple at least one of the first electrode and the second electrode to the controller. In some embodiments, the assembly comprises at least a three-wire configuration. In some embodiments, the controller is configured to pass an alternating current to the core and the second electrode. In some embodiments, the controller comprises a current source configured to pass an alternating current to the core and the second electrode. In some embodiments, the alternating current passed to the core and the second electrode originates from the same current source. In some embodiments, the alternating current can comprise a frequency of 5 kHz to 150 kHz.

In some embodiments of the present driver assemblies, the controller is configured to determine a change in at least one of the impedance and the voltage difference when the drill bit moves through biological material. In some embodiments, the controller is configured to compare the change in at least one of the impedance and the voltage difference to a threshold. In some embodiments, the controller comprises a threshold detector configured to compare the change in at least one of the impedance and the voltage difference to the threshold. In some embodiments, the threshold is adjustable. In some embodiments, the controller is configured to deactivate the motor if the change in at least one of the impedance and the voltage difference meets or exceeds the threshold. In some embodiments, the controller is configured to change a rotational speed of the motor if the change in at least one of the impedance and the voltage difference meets or exceeds the threshold.

In some embodiments of the present assemblies, the insulator comprises a non-conductive material. In some embodiments, the insulator comprises polytetrafluoroethylene. In some embodiments, the insulator comprises a thickness of 0.01 millimeters to 2 millimeters.

Some embodiments of the present assemblies comprise a display coupled to the controller and configured to display information relating to at least one of the impedance, the voltage between the core and the first electrode, and the change in at least one of the impedance and the voltage difference. In some embodiments, the display comprises at least one light emitting diode. In some embodiments, the display is configured to indicate information about a position of the drill bit based on the impedance, the voltage between the core and the first electrode, and the change in at least one of the impedance and the voltage difference.

Some embodiments of the present assemblies comprise a drill bit coupler configured to be coupled to the drill bit and to the drive shaft. In some embodiments, the drill bit coupler is insulated. In some embodiments, the drill bit coupler comprises an insulator.

Some embodiments of the present assemblies comprise at least one drill bit contact coupled to the drill bit and to the controller, the at least one drill bit contact configured to permit electrical communication between the controller and at least one of the core and the outer surface of the drill bit. In some embodiments, the drill bit contact is coupled to the drill bit by a commutating electrical connection. In some embodiments, the drill bit contact is slidably coupled to the drill bit. In some embodiments, the controller is configured to receive information from the core of the drill bit relating to at least one of current, voltage, impedance, and temperature. In some embodiments, the at least one drill bit contact is further configured such that the controller can receive information from the outer surface of the drill bit. In some embodiments, the information receivable from the outer surface relates to at least one of current, voltage, impedance, and temperature. In some embodiments, the drill bit contact comprises a non-conductive coating. In some embodiments, the drill bit contact comprises a dielectric.

Some embodiments of the present assemblies comprise a reference button coupled to the controller, the reference button being configured to set at least one of a reference impedance and a reference voltage difference, and the controller being configured to determine a change from at least one of the reference impedance and the reference voltage difference. In some embodiments, the reference button sets at least one of the reference impedance and the reference voltage difference when the reference button is engaged. In some embodiments, the controller is configured to set at least one of a reference impedance and a reference voltage difference automatically when the drill bit contacts a predetermined material within a target area. In some embodiments, the controller is configured to compare the change from at least one of the reference impedance and the reference voltage difference to a threshold. In some embodiments, the controller comprises a threshold detector configured to compare the change from at least one of the reference impedance and the reference voltage difference to the threshold. In some embodiments, the threshold is adjustable. In some embodiments, the controller is configured such that if the change from at least one of the reference impedance and the reference voltage difference meets or exceeds the threshold, the controller will cause the display to indicate at least one of the impedance, the voltage between the core and the first electrode, and the change in at least one of the impedance and the voltage difference. In some embodiments, the controller is configured to deactivate the motor if the change from at least one of the reference impedance and the reference voltage difference meets or exceeds the threshold. In some embodiments, the controller is configured to change a rotational speed of the motor if the change from at least one of the reference impedance and the reference voltage difference meets or exceeds the threshold.

In some embodiments, the present assemblies comprise an oscillator configured to produce a signal in the current. In some embodiments, the signal comprises a frequency of 10 kHz to 100 kHz. In some embodiments, the signal comprises a frequency of 50 kHz. In some embodiments, the controller further comprises a differential amplifier coupled to the drill bit and to the first electrode, the differential amplifier configured to output a voltage difference between the drill bit and the first electrode. In some embodiments, the differential amplifier comprises a high common mode rejection differential input amplifier. In some embodiments, the controller further comprises a multiplier coupled to the oscillator and to the differential amplifier, the multiplier configured to multiply a signal received from the differential amplifier with a signal received from the oscillator to down convert the voltage difference to a baseband frequency. In some embodiments, the multiplier is configured to produce a direct voltage. In some embodiments, the controller further comprises a gain amplifier coupled to the multiplier and configured to increase a voltage of the baseband frequency produced by the multiplier. In some embodiments, the gain amplifier is configured to increase the voltage of the baseband frequency by a factor of 1000. In some embodiments, the gain amplifier is configured to increase the voltage of the baseband frequency by a factor of 100 to 10,000. In some embodiments, the controller further comprises a low pass filter coupled to the gain amplifier and configured to attenuate a signal output by the gain amplifier that has a higher frequency than a cutoff frequency.

Some embodiments of the present methods comprise placing a first electrode of a driver assembly in or on a non-target area; moving a drill bit of the driver assembly through biological material toward a target area in biological material; and determining at least one of an impedance, a change in an impedance, a voltage difference, and a change in a voltage difference. In some embodiments, the methods comprise displaying a notification when at least one of the impedance, the change in an impedance, the voltage, and the change in a voltage difference meets or exceeds a threshold. In some embodiments, the methods comprise changing or stopping a rotational velocity of the drill bit when at least one of the impedance, the change in an impedance, the voltage, and the change in a voltage difference meets or exceeds a threshold. In some embodiments, the methods comprise placing a second electrode in or on the non-target area to form at least a three-wire configuration with the drill bit and the first electrode. In some embodiments, the methods comprise displaying a notification when at least one of an impedance, a change in a impedance, a voltage, and a change in a voltage meets or exceeds a threshold. In some embodiments, the methods comprise changing or stopping a rotational velocity of the drill bit when at least one of the impedance, the change in an impedance, the voltage, and the change in a voltage meets or exceeds a threshold. In some embodiments, the methods comprise removing the drill bit from the target area to permit access to the target area.

Some embodiments of the present methods (e.g., of determining at least one of a change in an impedance and a change in a voltage difference across biological material) comprise placing a first electrode of a driver assembly in or on a non-target area; moving a drill bit of the driver assembly through biological material toward a target area in biological material; setting at least one of a reference impedance and a reference voltage difference; and determining a change from at least one of the reference impedance and the reference voltage difference. In some embodiments, the methods comprise displaying a notification when the change from at least one of the reference impedance and the reference voltage difference meets or exceeds a threshold. In some embodiments, the methods comprise changing or stopping a rotational velocity of the drill bit when the change from at least one of the reference impedance and the reference voltage difference meets or exceeds a threshold. In some embodiments, the methods comprise placing a second electrode in or on the non-target area to form at least a three-wire configuration. In some embodiments, the methods comprise determining a change from at least one of the reference impedance and the reference voltage difference. In some embodiments, the methods comprise displaying a notification when the change from at least one of the reference impedance and the reference voltage difference meets or exceeds a threshold. In some embodiments, the methods comprise changing or stopping a rotational velocity when the change from at least one of the reference impedance and the reference voltage difference meets or exceeds a threshold. In some embodiments, the methods comprise removing the drill bit from the target area to permit access to the target area.

Some embodiments of the present drivers comprise a controller configured to determine at least one of an impedance and a voltage difference; a motor coupled to a power source and further coupled to the controller such that the controller can affect the motor's operation; a drive shaft coupled to the motor such that the motor can move the drive shaft; a trigger coupled to the controller and configured to activate the motor; and a first electrode configured to be coupled to the controller; where the driver is configured to be coupled to an intraosseous (IO) device and used, with the IO device, to determine at least one of a change in an impedance and a change in a voltage difference across biological material. In some embodiments, the driver comprises a two-wire configuration. In some embodiments, the driver is configured to generate an alternating current.

Some embodiments of the present drivers comprise a second electrode configured to be coupled to the controller; where the controller can pass a current to the second electrode, when the first and second electrodes are coupled to the controller, to permit the controller to determine at least one of an impedance and a voltage difference at least when the driver is used with an IO device in a medical procedure. In some embodiments, the drivers comprise at least a three-wire configuration. In some embodiments, the driver is configured to generate an alternating current. In some embodiments, the alternating current can comprise a frequency of 5 kHz to 150 kHz.

In some embodiments of the present drivers, the controller is configured to determine at least one of an impedance, a change in an impedance, a voltage difference, and a change in a voltage difference between when the first and second electrodes are coupled to the controller and the driver is used with an IO device in a medical procedure. In some embodiments, the controller is configured to compare at least one of the impedance, the change in an impedance, the voltage difference, and the change in a voltage difference to a threshold. In some embodiments, the controller comprises a threshold detector configured to compare at least one of the impedance, the change in an impedance, the voltage difference, and the change in a voltage difference to the threshold. In some embodiments, the threshold is adjustable. In some embodiments, the controller is configured to deactivate the motor if at least one of the impedance, the change in an impedance, the voltage difference, and the change in a voltage difference meets or exceeds the threshold. In some embodiments, the controller is configured to change a rotational speed of the motor if at least one of the impedance, the change in an impedance, the voltage difference, and the change in a voltage difference meets or exceeds the threshold. In some embodiments, at least one of the first electrode and the second electrode comprises an adhesive configured to adhere at least one of the first electrode and the second electrode to skin. In some embodiments, a patch connector configured to couple at least one of the first electrode and the second electrode to the controller.

Some embodiments of the present drivers comprise a display coupled to the controller. In some embodiments, the display comprises at least one light emitting diode.

Some embodiments of the present drivers comprise a drill bit coupler configured to be coupled to a drill bit and to the drive shaft. In some embodiments, the drill bit coupler is insulated. In some embodiments, the drill bit coupler comprises an insulator.

Some embodiments of the present drivers comprise a reference button coupled to the controller, the reference button being configured to set at least one of a reference impedance and a reference voltage difference, and the controller being configured to determine at least one of a change in impedance from the reference impedance and a change in voltage difference from the reference voltage difference when the driver is coupled to an IO device and used during a medical procedure. In some embodiments, the reference button sets at least one of the reference impedance and the reference voltage difference when the reference button is engaged. In some embodiments, the controller is configured to set at least one of the reference impedance and the reference voltage difference automatically when a condition is met. In some embodiments, the controller is configured to compare at least one of the change in impedance and the change in voltage difference to a threshold. In some embodiments, the controller comprises a threshold detector configured to compare at least one of the change in impedance and the change in voltage difference to the threshold. In some embodiments, the threshold is adjustable. In some embodiments, the controller is configured such that if at least one of the change in impedance and the change in voltage difference meets or exceeds the threshold, the controller will cause the display to change. In some embodiments, the controller is configured to deactivate the motor if at least one of the change in impedance and the change in voltage difference meets or exceeds the threshold. In some embodiments, the controller is configured to change a rotational speed of the motor if at least one of the change in impedance and the change in voltage difference meets or exceeds the threshold.

In some embodiments of the present drivers, the controller comprises an oscillator configured to produce a signal in the current. In some embodiments, the signal comprises a frequency of 10 kHz to 100 kHz. In some embodiments, the signal comprises a frequency of 50 kHz. In some embodiments, the controller further comprises a differential amplifier. In some embodiments, the differential amplifier comprises a high common mode rejection differential input amplifier. In some embodiments, the controller further comprises a multiplier coupled to the oscillator and to the differential amplifier, the multiplier configured to multiply a signal received from the differential amplifier with a signal received from the oscillator to down convert a voltage to a baseband frequency. In some embodiments, the multiplier is configured to produce a direct voltage. In some embodiments, the controller further comprises a gain amplifier coupled to the multiplier and configured to increase a voltage of the baseband frequency produced by the multiplier. In some embodiments, the gain amplifier is configured to increase the voltage of the baseband frequency by a factor of 1000. In some embodiments, the gain amplifier is configured to increase the voltage of the baseband frequency by a factor of 100 to 10,000. In some embodiments, the controller further comprises a low pass filter coupled to the gain amplifier and configured to attenuate a signal output by the gain amplifier that has a higher frequency than a cutoff frequency.

Some embodiments of the present drill bits comprise an outer surface; a core disposed inside the outer surface; and an insulator disposed between the core and the outer surface configured to prevent electrical communication between the core and the outer surface, where the outer surface, the insulator, and the core cooperate to form at least one tip of the drill bit configured to penetrate bone, and where the drill bit is configured to be coupled to a driver and used to determine at least one of a change in impedance and a change in voltage difference across biological material during a medical procedure. In some embodiments, the drill bit is configured to be coupled to a drive shaft of a driver by a commutating electrical connection. In some embodiments, the drill bit is configured to be coupled to the drive shaft by a gear box bearing, the gear box bearing configured to permit a commutating electrical connection between the drill bit and a drive shaft of a driver. In some embodiments, the insulator comprises a non-conductive material. In some embodiments, the insulator comprises polytetrafluoroethylene. In some embodiments, the insulator comprises a thickness of 0.01 millimeters to 2 millimeters. In some embodiments, a portion of the core is exposed at the tip of the drill bit.

Any embodiment of any of the driver assemblies, drivers, drill bits, and methods can consist of or consist essentially of—rather than comprise/include/contain/have—any of the described elements, features, and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures illustrate the described elements using graphical symbols that will be understood by those of ordinary skill in the art. The embodiments of the present driver assemblies, drivers, drill bits, and their components shown in the figures are drawn to scale for at least the embodiments shown.

DESCRIPTION OF ILLUSTRATIVE EMBODIMENTS

Figure 1A:
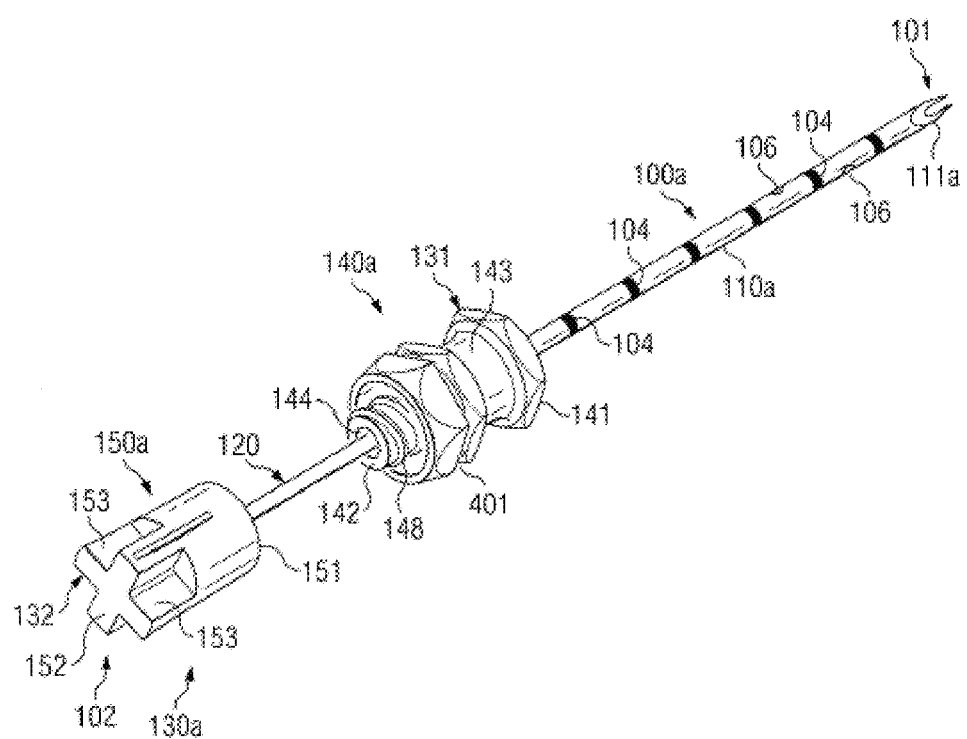
FIG. 1A depicts a perspective view of a prior art intraosseous device having a cannula and a stylet.

The term "coupled" is defined as connected, although not necessarily directly, and not necessarily mechanically. Two items are "couplable" if they can be coupled to each other. Unless the context explicitly requires otherwise, items that are couplable are also decouplable, and vice-versa. One non-limiting way in which a first structure is couplable to a second structure is for the first structure to be configured to be coupled to the second structure. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus or kit, or a component of an apparatus or kit, that "comprises," "has," "includes" or "contains" one or more elements or features possesses those one or more elements or features, but is not limited to possessing only those elements or features. Likewise, a method that "comprises," "has," "includes" or "contains" one or more steps possesses those one or more steps, but is not limited to possessing only those one or more steps. Additionally, terms such as "first"

and "second" are used only to differentiate structures or features, and not to limit the different structures or features to a particular order.

The term "determine" (and any form of determine, such as "determines," "determined," and "determining") is used broadly throughout this disclosure to include the receiving or gathering of information from an area and any resulting calculations with and/or manipulations of such information and should include terms (and derivatives of such terms) such as detecting, measuring, identifying, receiving, and similar terms.

Further, a system (such as one of the present driver assemblies), a device (such as one of the present drivers or one of the present drill bits), or a component of a device (such as a controller or sensor of one of the present drivers) that is configured in a certain way is configured in at least that way, but can also be configured in other ways than those specifically described.

Various types of coupler assemblies incorporating teachings of the present disclosure may be satisfactorily used to releasably engage one end of a shaft extending from a driver with one end of an intraosseous device. For some embodiments, the powered driver may include a driveshaft having one end with a generally hexagonal cross section operable to be releasably engaged with a latch mechanism disposed in one end of a coupler assembly. For some embodiments, a coupler assembly incorporating teachings of the present disclosure may be referred to as a "hands free" coupler, a quick disconnect or quick release coupler and/or port assembly.

Various types of coupler assemblies incorporating teachings of the present disclosure may be satisfactorily used to releasably engage one end of a shaft extending from a driver with one end of an intraosseous device. For some embodiments, the powered driver may include a driveshaft having one end with a generally hexagonal cross section operable to be releasably engaged with a latch mechanism disposed in one end of a coupler assembly. For some embodiments, a coupler assembly incorporating teachings of the present disclosure may be referred to as a "hands free" coupler, a quick disconnect or quick release coupler and/or port assembly.

Embodiments of the present powered drivers may be used to insert an IO device into a selected target area or target site in ten seconds or less. However, various teachings of the present disclosure are not limited to use with powered drivers. Manual drivers and spring powered drivers may also be used with IO devices (such as embodiments of the present drill bits) incorporating teachings of the present disclosure.

Examples of manual drivers are shown in co-pending patent application Ser. No. 11/042,912 entitled Manual Intraosseous Device filed Jan. 25, 2005 (published as US 2005/0165404). The term "fluid" may be used in this application to include liquids such as, but not limited to, blood, water, saline solutions, IV solutions, plasma, or any mixture of liquids, particulate matter, dissolved medication, and/or drugs associated with biopsy or aspiration of bone marrow or communication of fluids with bone marrow or other target sites. The term "fluid" may also be used in this patent application to include any body fluids and/or liquids containing particulate matter such as bone marrow and/or cells which may be withdrawn from a target area.

The terms "harvest" and "harvesting" may be used in this application to include bone and/or bone marrow biopsy and bone marrow aspiration. Bone and/or bone marrow biopsy (sometimes referred to as "needle biopsy") may be generally described as removing a relatively small piece or specimen of bone and/or bone marrow from a selected target area for biopsy purposes. Bone marrow aspiration (sometimes referred to as "bone marrow sampling") may be generally described as removing larger quantities of bone marrow from a selected target area. Relatively large quantities of bone marrow may be used for diagnostic, transplantation, and/or research purposes. For example some stem cell research techniques may require relatively large quantities of bone marrow.

The term "insertion site" may be used in this application to describe a location on a bone at which an intraosseous device may be inserted or drilled into the bone and associated bone marrow. Insertion sites are generally covered by skin and soft tissue. The term "target area" refers to any location on or within biological material, such as the biological material of a living human being.

The term "intraosseous (IO) device" may be used in this application to include, but is not limited to, any hollow needle, hollow drill bit, penetrator assembly, bone penetrator, catheter, cannula, trocar, stylet, inner penetrator, outer penetrator, IO needle, biopsy needle, aspiration needle, IO needle set, biopsy needle set or aspiration needle set operable to access or provide access to an intraosseous space or interior portions of a bone. Such IO devices may be formed, at least in part, from metal alloys such as 304 stainless steel and other biocompatible materials associated with needles and similar medical devices.

Embodiments of the present driver assemblies can be included in medical procedure trays such as those disclosed in International Patent Application No. PCT/US2007/078207 (published as WO 2008/033874).

The devices and components shown in FIGS. 1A to 7C are prior art devices and components, and the following description of them is provided to give the reader context for the types of devices and components that can be used consistently with embodiments of the present driver assemblies, drivers, and methods.

Referring now to the drawings, and more particularly to FIG. 1A, shown therein and designated by the reference numeral 100 is one embodiment of the present intraosseous (IO) needle sets or aspiration needle sets. Aspiration needle set 100 comprises a hollow outer penetrator or cannula 110*a*, a corresponding inner penetrator or stylet (or trocar) 120, and a hub assembly 130*a*. In the embodiment shown, first end 111*a* of cannula 110*a* and first end 121 of stylet 120 are operable or configured to penetrate a bone and associated bone marrow. Various features of first end 111*a* of cannula 110*a* and first end 121 of stylet 120 are shown in more detail in. First end 101 of IO needle set 100 corresponds generally with first end 111*a* of cannula 110*a* and first end 121 of stylet 120.

In the embodiment shown, cannula 110*a* includes a plurality of markings 104 disposed on exterior portions of the cannula. Markings 104 may be referred to as "positioning marks" or "depth indicators," and may be used to indicate the depth of penetration of needle set 100 into a bone and associated bone marrow. In some embodiments, cannula 110*a* may have a length of approximately sixty (60) millimeters and/or a nominal outside diameter of approximately 0.017 inches (e.g., corresponding generally to the dimensions of a sixteen (16) gauge needle). Cannula 110*a* and/or stylet 120 may be formed from stainless steel or other suitable biocompatible materials. In some embodiments, markings 104 are spaced at one (1) centimeter intervals on exterior portions of cannula 110*a*. In some embodiments, one or more side ports 106 may be formed in exterior portions of cannula 110*a* spaced from first end 111*a*.

Hub assembly 130a may be configured and/or used to releasably dispose stylet 120 within the longitudinal bore or lumen of cannula 110a. In the embodiment shown, hub assembly 130a includes a first hub 140a and a second hub 150a. A second end of cannula 110a, opposite from first end 111a, may be securely engaged with hub 140a. The second end of stylet 120, opposite from first end 121, may be securely engaged with the first end of hub 150a. As shown in FIG. 1A, cannula 110a may extend longitudinally from first end 141 of hub 140a. Stylet 120 may also extend from the first end of hub 150a. The second end of hub 140a may include a standard Luer lock fitting which may be releasably engaged with a corresponding Luer lock fitting disposed within the first end of second hub 150a. The Luer lock fitting disposed on the second end of hub 140a may be in fluid communication with the bore or passage in cannula 110a, and may be operable to be releasably engaged with a standard syringe type fitting and/or a standard intravenous (IV) connection. In the embodiment shown, hub 150a includes second end 152 that generally corresponds with second end 132 of hub assembly 130a and second end 102 of IO needle set 100. Hub 140a may include first end 141 which may generally correspond with first end 131 of hub assembly 130a. Cannula 110a may extend longitudinally from first end 141 of hub 140a and first end 131 of hub assembly 130.

Figure 6A:
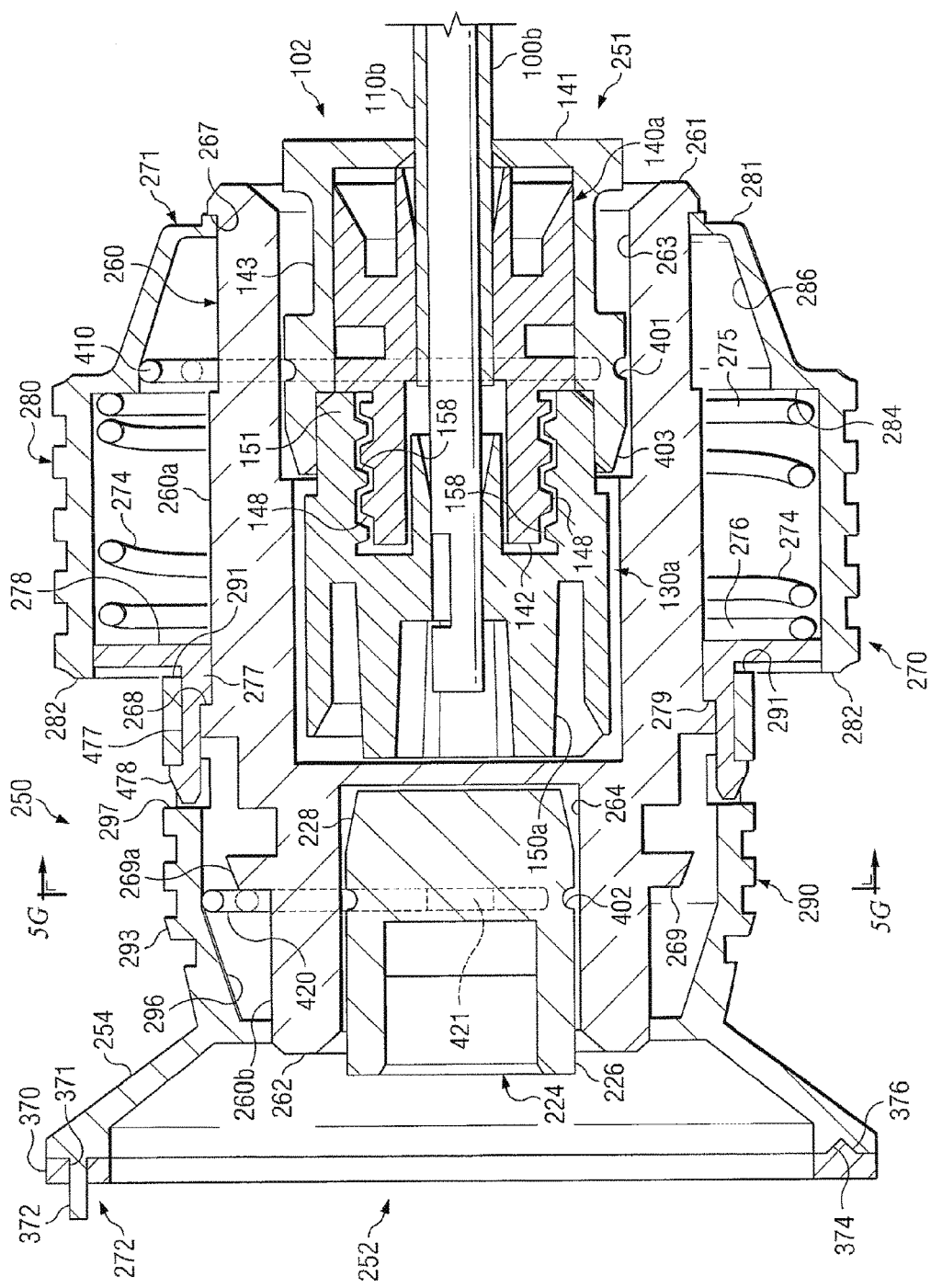
FIGS. 6A-6C depict various views of the coupler assembly of FIG. 3.
Figure 6B:
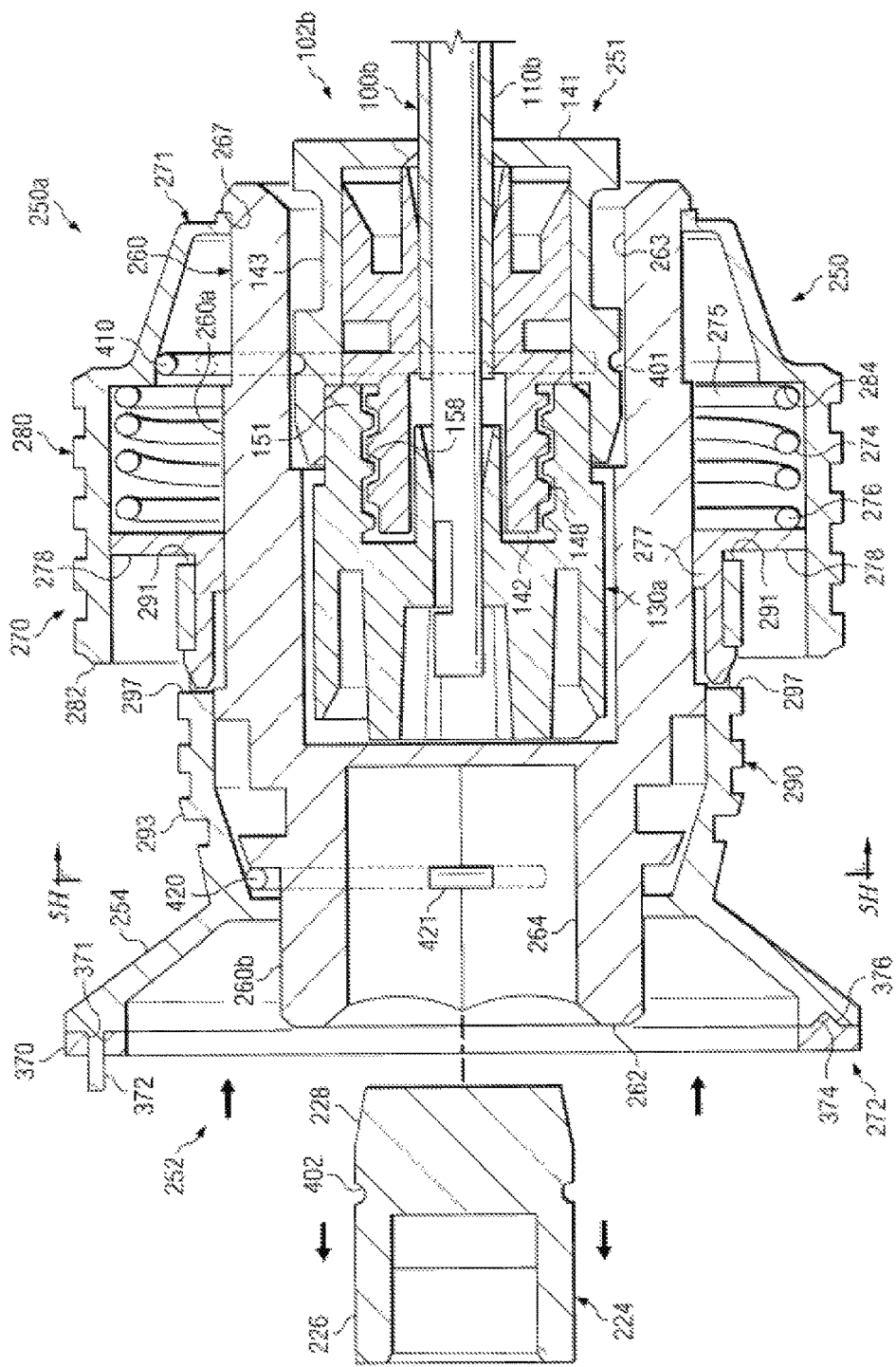

In the embodiment shown, the second end of a hub assembly may be operable to be disposed within a receptacle formed in a coupler assembly, as described in more detail below. One feature of the present disclosure may include forming a hub assembly which may be releasably engaged within a first receptacle disposed in a first end of a coupler assembly (e.g., receptacle 263 proximate first end 261 of elongated core 260 as shown in FIGS. 6A-6B). The dimensions and configuration of receptacle 263 may be selected to prevent rotation of hub 150a relative to hub 140a if hub assembly 130a is disposed in receptacle 263 (e.g., while inserting (rotating) an IO device into a bone and associated bone marrow). A powered driver may be releasably engaged with a second receptacle disposed in a second end of the coupler assembly (e.g., receptacle 264 proximate second end 262 of elongated core 260 as shown in FIGS. 6A-6B).

In the embodiment shown, intraosseous device or aspiration needle set 100a includes first end 151 of hub 150a spaced from second end 142 of hub 140a. Portions of stylet 120 extending from first end 151 of hub 150a are shown slidably disposed within lumen or longitudinal bore 118 of cannula 110a. Hub assembly 130a may include first end 131 which may correspond generally with first end 141 of hub 140a. Hub assembly 130a may also include second end 132 which may correspond generally with second end 152 of hub 150a and second end 102 of hub assembly 130a, as shown. Cannula 110a may be attached to and extend from first end 141 of hub 140a. Second end 142 of hub 140a may include one-half a typical Luer lock connection or fitting operable to be releasably engaged with corresponding portions of a Luer lock connection or fitting disposed in first end 151 of second hub 150a. For embodiments such as the one shown in FIG. 1A, first end 131 of hub assembly 130a may correspond with first end 141 of first hub 140a. Second end 152 of second hub 150a may correspond with second end 132 of hub assembly 130a and second end 102 of aspiration needle set 100a.

At least one portion of hub assembly 130a may have a generally hexagonal cross section operable to be received within the generally hexagonal cross section of receptacle 263 disposed proximate first end 251 of coupler assembly 250, as shown in FIGS. 6A-6B. For some embodiments, portions of first hub 140a disposed adjacent to reduced outside diameter portion 143 may have generally hexagonal cross sections, as shown in FIG. 1A. In other embodiments, various cross sections other than hexagonal may be satisfactorily used to releasably engage a powered driver with one end of a coupler assembly and an intraosseous device with an opposite end of the coupler assembly. Aspiration needle sets may include a stylet, stylet or penetrator in combination with an associated cannula, catheter or outer penetrator. However, biopsy needles formed in accordance with teachings of the present disclosure may or may not include a stylet, stylet or inner penetrator.

Hub 140a may include second end 142 with opening 144 formed therein. A passageway may extend from second end 142 towards first end 141 of hub 140a, as illustrated in FIGS. 6A-6B. A passageway may be operable to communicate fluids with lumen 118 of cannula 100a. Second end 142 of hub 140 may include various features of a conventional Luer lock connection or fitting, including threads 148, and corresponding threads 158 may be formed within first end 151 of hub 150a, as shown in FIGS. 6A-6B.

For some applications hub 140a and hub 150a may, for example, be formed using injection molding techniques. For such embodiments hub 140a may include reduced outside diameter portion 143 disposed between first end 141 and second end 142. In a similar manner a plurality of void spaces or cutouts 153 may be formed in hub 150a adjacent to and extending from second end 152 in the direction of first end 151. The configuration and dimensions of reduced diameter portion 143 and/or cutouts 153 may be varied to optimize associated injection molding techniques and at the same time provide required configurations, dimensions and material strength to allow associated hub assembly 130a to function as described in this disclosure.

In some embodiments, tip 123 of stylet 120 may be disposed relatively close to a tip of cannula 110a. For some applications, first end 121 of stylet 120 and first end 111a of cannula 110a may be ground at the same time to form adjacent cutting surfaces. Grinding ends 111a and 121 at the same time may result in forming a single cutting unit to form generally matching cutting edges. Other types of cutting surfaces formed in accordance with teachings of the present disclosure may be discussed later (e.g., as described with reference to FIGS. 1B-1D).

Figure 1B:
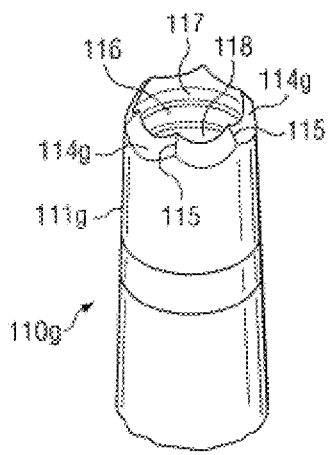
FIG. 1B depicts a perspective view of another prior art cannula.
Figure 1C:
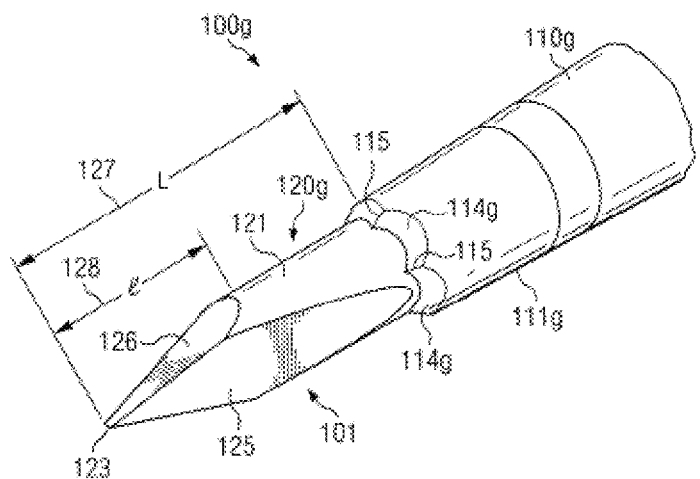
FIGS. 1C and 1D depict perspective views of a prior art IO device having a stylet disposed in the cannula of FIG. 1B.
Figure 1D:
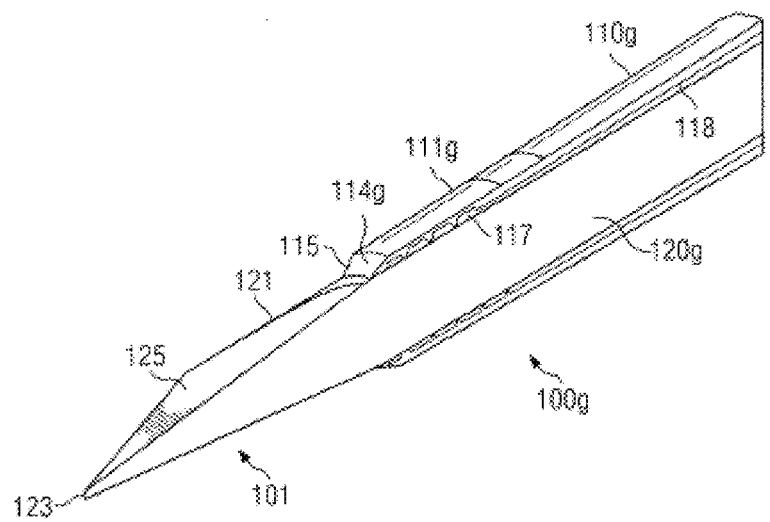

FIGS. 1B-1D show a second example of cutting surfaces and tips which may be formed adjacent to the ends of a cannula and/or an associated stylet in the present embodiments. In the embodiment shown, outer penetrator or cannula 110g may include first end 111g having a plurality of cutting surfaces 114g formed adjacent to opening 116 in first end 111g. Opening 116 may communicate with and form a portion of an associated longitudinal bore or lumen 118. For some applications cutting surfaces 114g may be formed using electrical discharge machining (EDM) techniques or otherwise, as described in WO 2008/033874. In the embodiment shown, first end 111g has a generally tapered configuration or reduced outside diameter as compared with other portions of cannula 110g In other embodiments, first end 111g has an outside diameter that is equal to the outside diameter of other portions of cannula 110g (e.g., cannula 110g can have a constant outside diameter along the entire length of the cannula). Cutting surfaces 114g may, for example, be formed using machine grinding techniques. In some embodiments, such as the one shown, end 111g of cannula 110g may include six ground cutting surfaces 114g with respective crowns 115 therebetween. Forming a biopsy needle set and/or biopsy needle with tapered end 111g and a plurality of cutting surfaces 114g and crowns 115 may provide improved drilling performance (e.g., relative to others configurations) when the resulting biopsy needle set and/or biopsy needle is used with a powered driver in accordance with teachings of the present disclosure. For some applications, a helical groove 117 may be formed within longitudinal bore 118 proximate opening 116. Helical groove 117 may assist with retaining a biopsy specimen or a bone marrow specimen within longitudinal bore 118. For example, a single thread may be disposed within the longitudinal bore or lumen of the cannula such that the helical groove 117 is defined between turns of the thread. Various techniques and procedures may be satisfactorily used to place the single thread or otherwise form the helical groove, as described WO 2008/033874.

As shown in FIG. 1C, a biopsy needle set 100g may include cannula or outer penetrator 110g with stylet or inner penetrator 120g slidably disposed therein. The proximal ends of cannula 110g and stylet 120g may be similar to those of cannula 110a and stylet 120 depicted in FIG. 1A (e.g., may include hubs 140a and 150a, respectively). For some applications first end 101 of biopsy needle set 100g may minimize damage to skin and soft body tissue at an insertion site. For some applications inner penetrator or stylet 120g may include first end 121 having a plurality of cutting surfaces 125 and 126 formed on exterior portions thereof extending from associated tip 123 towards second end of stylet or inner penetrator 120g. For some applications one or more cutting surfaces 125 may be formed having length 127 extending from tip 123 to associated cutting surfaces 114g in associated cannula 110g. One or more cutting surfaces 126 may be formed adjacent to each cutting surface 125 with second length 128. First length 127 may be greater than second length 128. As shown, lengths 127 and 128 are measured parallel to the central longitudinal axis of stylet 120g. The ratio of first length 127 and second length 128 may be varied in accordance with teachings of the present disclosure to provide optimum performance for penetrating a selected bone and associated bone marrow. Additional details of some embodiments of first end 101 are described in WO 2008/033874.

Figure 2:
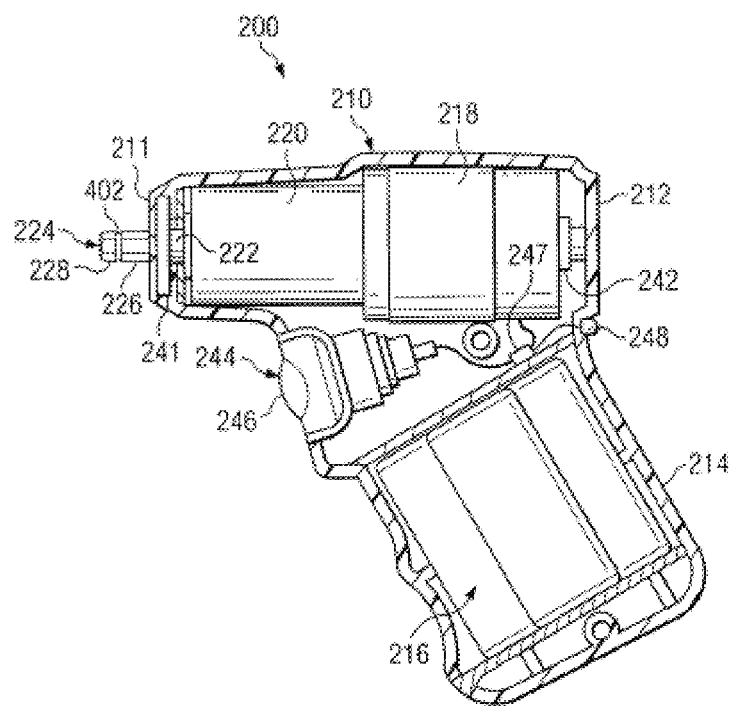
FIG. 2 depicts a cross-sectional side view of a prior art driver that may be modified to have one of the present sensors and, thus, become one of the present drivers.

FIG. 2 depicts a cross-sectional view of one embodiment of a driver that can be used as an example for an embodiment of the present drivers with sensors and methods and kits comprising such drivers. In the embodiment shown, powered driver 200 may be used to insert intraosseous devices into a bone and associated bone marrow. Powered driver 200 may include housing 210 having a general configuration similar to a small pistol defined in part by handle 214. Various components associated with powered driver 200 may be disposed within housing 210 (e.g., handle 214). For example a power source such as battery pack 216 may be disposed within handle 214. Housing 210 may be formed from relatively strong, heavy duty polymeric materials such as polycarbonate or other satisfactory materials. For some applications housing 210 may be formed in two halves (not expressly shown) which may be joined together with a fluid tight seal to protect various components of powered driver 200 disposed therein.

Figure 6C:
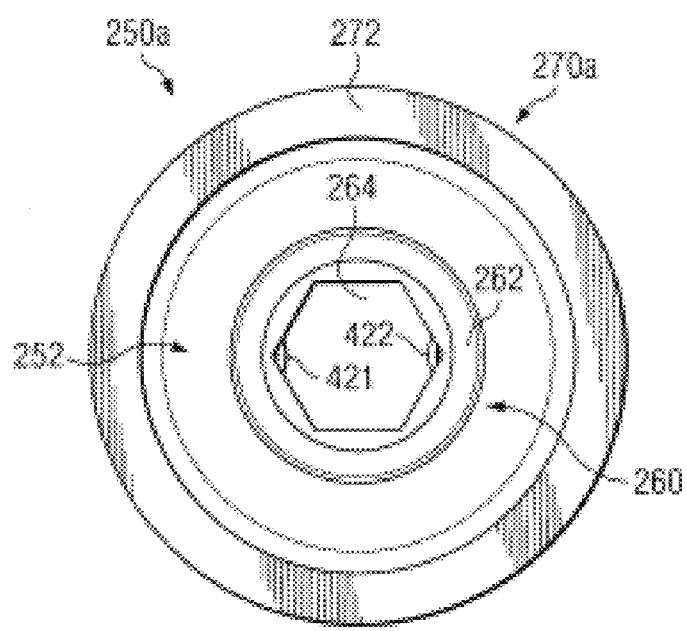

Motor 218 and gear assembly 220 may be disposed within portions of housing 210 adjacent to handle 214. Motor 218 and gear assembly 220 may be generally aligned with each other. Motor 218 may be rotatably engaged with one end of gear assembly 220. Drive shaft 222 may be rotatably engaged with and extend from another end of gear assembly 220 opposite from motor 218. For some applications both motor 218 and gear assembly 220 may have generally cylindrical configurations. Distal end or first end 211 of housing 210 may include an opening with portions of drive shaft 222 extending through the opening, as shown. For some applications, end 224 or the portion of drive shaft 222 extending from first end 211 of housing 210 may have a generally hexagonal cross section with surfaces 226 disposed thereon. Receptacle 263 disposed in second end 252 of coupler assembly 250 may have a matching generally hexagonal cross section, as shown in FIGS. 6A-6C.

Surfaces 226 may extend generally parallel with each other and parallel with respect to a longitudinal axis or rotational axis of drive shaft 222. One or more tapered surfaces 228 may also be formed on end 224 to assist with releasably engaging powered driver 200 with coupler assembly 250. Embodiments of powered driver 200 include speed reduction ratios, for example, of between 60:1 and 80:1, resulting in drive shaft RPMs that are reduced relative to motor RPMs. Coupler assemblies having corresponding openings or receptacles may be releasably engaged with end 224 extending from first end 211 of powered driver 200. For example, end 224 extending from first end 211 of housing 210 may be releasably engaged with receptacle 264 disposed proximate second end 252 of coupler assembly 250, as shown in FIGS. 6A-6B.

For some applications thrust bearing 241 may be disposed between first end or distal end 211 of housing 210 and adjacent portions of gear assembly 220. Thrust bearing 242 may be disposed between second end or proximal end 212 of housing 210 and adjacent portions of motor 218. Thrust bearings 241 and 242 may limit longitudinal movement of motor 218, gear assembly 220 and drive shaft 222 within associated portions of housing 210. Trigger assembly 244 may also be disposed within housing 210 proximate handle 214. Trigger assembly 244 may include trigger or contact switch 246. Motor 218 may be energized and deenergized by alternately depressing and releasing trigger 246. Electrical circuit board 247 may also be disposed within housing 210. Electrical circuit board 247 may be electrically coupled with trigger assembly 244, motor 218, power supply 216 and indicator light 248. For some applications indicator light 248 may be a light emitting diode (LED) or a small more conventional light bulb. For some applications indicator light 248 may be activated when ninety percent (90%) of electrical storage capacity of battery pack 216 has been used. The configuration and dimensions of an intraosseous device formed in accordance with teachings of the present disclosure may vary depending upon respective intended applications for each intraosseous device. For example the length of a biopsy needle formed in accordance with teachings of the present disclosure may vary from approximately five (5) millimeters to thirty (30) millimeters.

Coupler assemblies incorporating teachings of the present disclosure may function as "quick release mechanisms" operable to engage and disengage an IO device from a powered driver (e.g., a driver disposed within a flexible containment bag or sterile sleeve). Such coupler assemblies may allow rotation of an IO device (e.g., biopsy needle or needle set) without damage to the flexible containment bag or sterile sleeve. One end of the coupler assembly may be operable to form a fluid seal or fluid barrier with adjacent portions of the containment bag or sterile sleeve. A coupler assembly incorporating teachings of the present disclosure may also be described as a port assembly attached to a containment bag. Such port assemblies may allow easy engagement or disengagement of a powered driver from an IO device and at the same time allow the powered driver to "power in and power out" an IO device from an insertion site.

Figure 3:
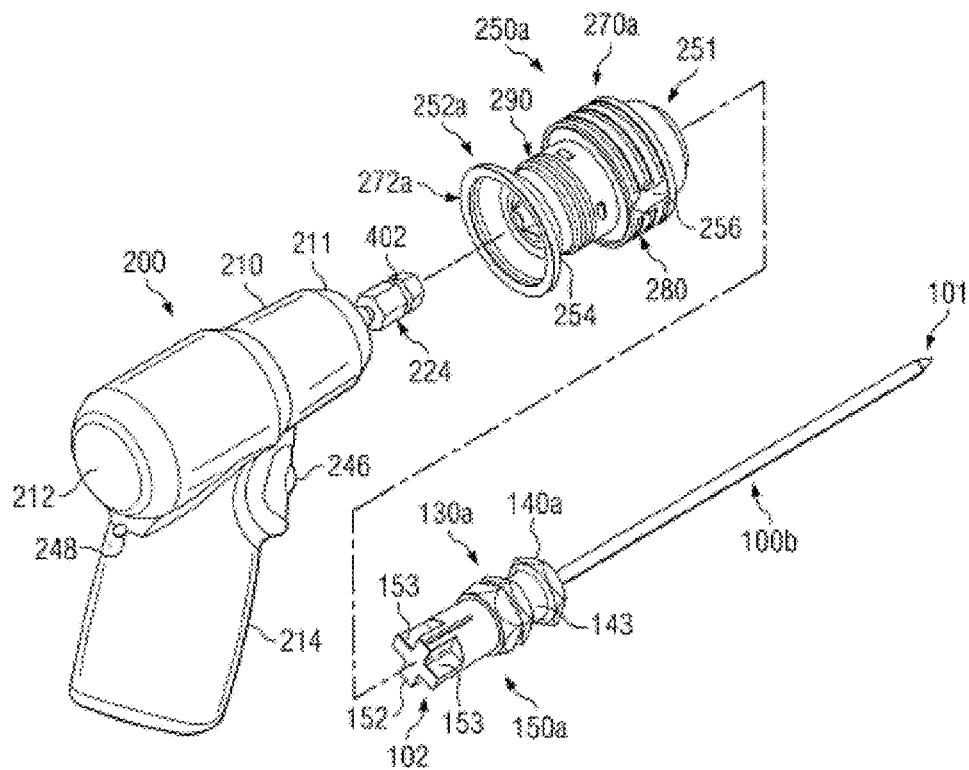
FIG. 3 depicts a perspective view of the driver of FIG. 2 with a prior art coupler assembly and a prior art IO device.
Figure 4:
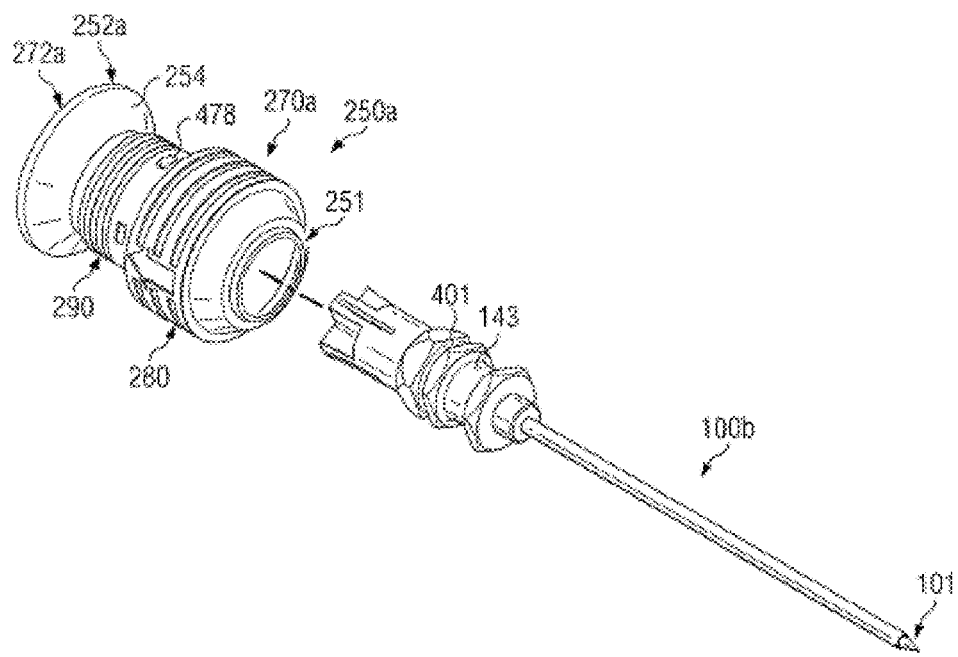
FIG. 4 depicts the coupler assembly and IO device of FIG. 3.
Figure 5:
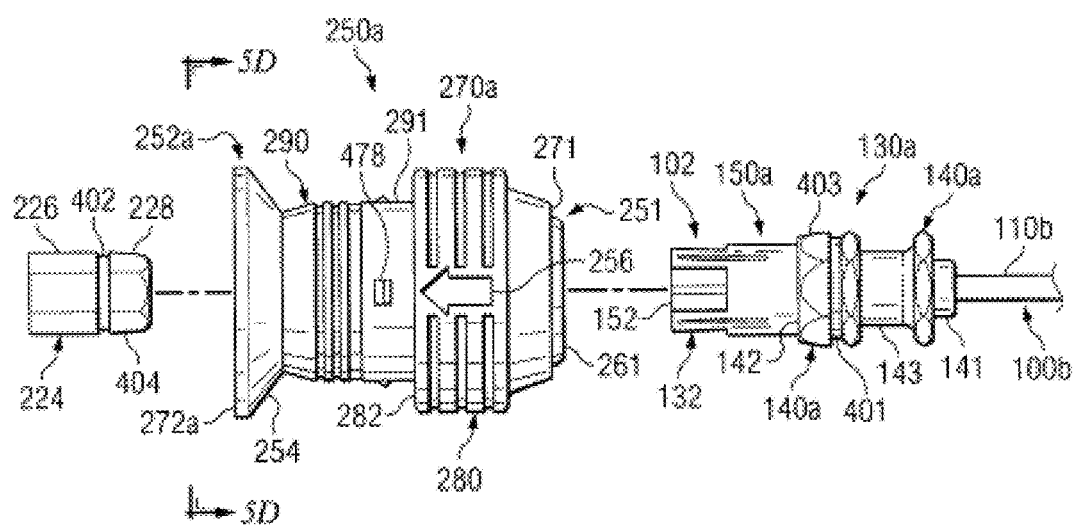
FIG. 5 depicts portions of the driver of FIG. 2 and the coupler assembly and a portion of the IO device of FIG. 3.

FIGS. 3-6C depict an example of a coupler assembly 250 suitable for some embodiments of the present assemblies and kits. FIGS. 3-5 are perspective views showing various views of powered driver 200, coupler assembly 250a, and intraosseous device 100b that is substantially similar to device 100a with the exception that device 100b does not include markings 104. Coupler assembly 250a includes a first end 251 operable to be releasably engaged with one end of an intraosseous device such as, but not limited to, second end 102 of biopsy needle set 100b. Coupler assembly 250a also includes a second end 252 operable to be releasably engaged with a portion of a drive shaft extending from a powered driver, such as, but not limited to, end 224 of drive shaft 222 extending from first end 211 of housing 210 of powered driver 200. Though not depicted here, second end 252 of coupler assembly 250 may be securely engaged with an opening in a containment bag or sterile sleeve, as described in WO 2008/033874.

Coupler assemblies incorporating various teachings of the present disclosure may be placed in a medical procedure tray or kit with one end down and an opposite end looking up to allow "hands free" releasable engagement with a powered driver or a manual driver. For example, coupler assembly 250a may be disposed in medical procedure tray with first end 251 facing downward and second end 252 facing up such that end 224 of drive shaft 222 (of driver 200) may be inserted into and releasably engaged with second end 252 of coupler assembly 250 without requiring an operator or user to physically contact or manipulate any portion of coupler assembly 250a. As described below, coupler 250a may include a "hands free" latching mechanism.

In the embodiment shown, coupler assembly 250a may include elongated core 260 with housing assembly 270 slidably disposed on exterior portions of elongated core 260. Housing assembly 270/270a may include first end 271 and second end 272 which may be generally aligned with respective first end 261 and respective second end 262 of elongated core 260. For some applications, elongated core 260 may have a generally cylindrical configuration defined in first exterior portion 260a and second exterior portion 260b with various shoulders and/or recesses formed thereon. For some embodiments first exterior portion 260a may have a larger diameter than second exterior portion 260b. Housing assembly 270 may be described as having a generally hollow, cylindrical configuration defined in part by first housing segment 280 and second housing segment 290. The first end of housing segment 280 may generally correspond with first end 271 of housing assembly 270. The second end of second housing segment 290 may generally correspond with second end 272 of housing assembly 270. First end 291 of second housing segment 290 may be described as having a generally cylindrical configuration with an outside diameter smaller than the adjacent inside diameter of second end 282 of first housing segment 280. Second housing segment 290 may slide longitudinally from a first position (FIG. 6A) to a second position (FIG. 6B) within second end 282 of first housing segment 280 to release one end of a drive shaft engaged with second end 252 of coupler assembly 250.

A biasing mechanism such as coiled spring 274 may be disposed around exterior portion 260a of generally elongated core 260. First end 275 of coiled spring 274 may contact annular shoulder 284 formed on interior portions of first housing segment 280. Second end 276 of coiled spring 274 may contact annular shoulder 278 disposed proximate first end 291 of second housing segment 290. Coil spring 274, annular shoulder 284 and annular shoulder 278 may cooperate with each other to generally maintain first housing segment 280 and second housing segment 290 in a first extended position relative to each other. Other biasing mechanisms such as, but not limited to, leaf springs and bellows (not expressly shown) may also be disposed between annular shoulder 284 and annular shoulder 278. Annular shoulder 278, associated with second end 276 of coiled spring 274, may extend radially outward from generally cylindrical ring 277. Generally cylindrical ring 277 may be slidably and rotatably disposed on exterior portion 260a of elongated core 260. Annular shoulder 279 may be disposed on interior portions of generally cylindrical ring 277 and may extend radially inward toward adjacent portions of elongated core 260. Annular shoulder 268 may be formed on exterior portion 260a of elongated core 260 intermediate first end 261 and second end 262. The configuration and dimensions of annular shoulder 268 and annular shoulder 279 are selected to be compatible with each other such that engagement between annular shoulder 279 of generally cylindrical ring 277 with annular shoulder 268 of elongated core 260 may limit movement of second housing segment 290 longitudinally in the direction of second end 262 of elongated core 260.

For some applications a plurality of flexible collets or fingers 477 may extend from generally cylindrical ring 277 opposite from annular shoulder 278. Respective collet heads 478 may be formed on the end of each collet 477 opposite from annular shoulder 278. The dimensions and configuration of collet heads 478 may be selected to be received within respective slots or openings 297 formed in second housing 290. During manufacture of coupler assembly 250a, each collet head 478 may be disposed within respective slot or opening 297 to securely engage generally cylindrical ring 277 and annular shoulder 278 proximate first end 291 of second housing segment 290. As a result, second housing segment 290 and annular shoulder 278 may generally move as a single unit relative to elongated core 260 and first housing segment 280. During disengagement of an intraosseous device from first end 251 of coupler assembly 250a, first housing segment 280 may move or slide longitudinally toward second housing segment 290. In a similar manner, second housing segment 290 may move or slide longitudinally toward first housing segment 280 during disengagement of a powered driver from second end 252 of coupler assembly 250a.

Annular shoulder 267 may be formed on exterior portions of elongated core 260 proximate first end 261. Annular shoulder 267 may engage portions of first end 271 of housing 270 to limit longitudinal movement of first housing segment 280 during longitudinal movement of second housing segment 290 towards first end 261 of elongated core 260 during disengagement of a powered driver from second end 252 of coupler assembly 250a. As previously noted, annular shoulder 268 may be formed on exterior portions of elongated core 260 between first end 261 and second end 262. Engagement between annular shoulder 268 and annular shoulder 279 of generally cylindrical ring 277 may limit movement of second housing segment 290 toward second end 262 of elongated core 260. Contact between spring 274 and annular shoulder 278 and annular shoulder 284 of first housing segment 280 may limit the longitudinal movement of first housing segment 280 in the direction of second end 262 of elongated core 260 during disengagement of an intraosseous device from first end 251 of coupler assembly 250a.

Generally cylindrical ring 277 and attached annular shoulder 279 may slide longitudinally on exterior portions of annular core 260 between annual shoulder 268 and annular shoulder 267. First housing segment 280 may move longitudinally toward second end 262 of elongated core 260 to release one end of intraosseous device from engagement with first end 251 of coupler assembly 250a. In a similar manner, second housing segment 290 may move longitudinally toward first end 261 of elongated core 260 to release one end of a drive shaft extending from a powered driver engaged with second end 252 of coupler assembly 250a. A wide variety of latches and latch mechanisms may be satisfactorily used to releasably engage one end of an intraosseous device within a first end of a coupler assembly incorporating teachings of the present disclosure. In a similar manner, a wide variety of latches and latch mechanisms may be satisfactorily used to releasably engage one end of a drive shaft extending from a powered driver or manual driver within a second end of the coupler assembly incorporating teachings of the present disclosure.

For embodiments represented by coupler assembly 250a, first latch 410 may be disposed on exterior portions of elongated core 260 proximate receptacle 263 adjacent to first end 261 to releasably engage one end of an IO device such as second end 102 of biopsy needle set 100b within receptacle 263 of coupler assembly 250a. Second latch mechanism 420 may be disposed on exterior portions of elongated core 260 proximate receptacle 264 adjacent to second end 262 to releasably engage one end of a drive shaft with second end 252 of coupler assembly 250a. Second latch 420 may be used to releasably engage one portion of a drive shaft such as end 224 of drive shaft 222 extending from powered driver 200 within second end 252 of coupler assembly 250a. Latch 410 may releasably engage an intraosseous device with first end 251 of coupler assembly 250a and substantially the same latch 420 may releasably engage a powered driver with second end 252 of coupler assembly 250a.

For some applications, latches 410 and 420 may have similar configurations such as a general "omega" shape (e.g., latch 420). However, latch 410 may have larger dimensions corresponding generally with exterior portion 260a of elongated core 260. Latch 420 may have smaller dimensions corresponding generally with exterior portion 260b of elongated core 260. Various features of the present disclosure may be described with respect to latch mechanism 420 along with adjacent portions of second housing segment 290 and exterior portion 260b of elongated core 260. Respective detents 421 and 422 may be formed on opposite ends of generally omega shaped latch 420. In a similar manner, respective detents (not expressly shown) may be formed on the ends of generally omega shaped latch 410. The configuration and dimensions of detents 421 and 422 may be compatible with placing each detent 421 and 422 in a respective slot or opening extending between exterior portion 260b of elongated core 260 to interior portions of receptacle 264 disposed proximate second end 252 of coupler assembly 250a. Latch 420 may have a first position in which portions of detents 421 and 422 may extend through the respective slots. The dimensions and configuration of detent 421 and 422 may be operable to be securely engaged with annular groove 402 formed in end 224 of powered driver 200. In a similar manner, respective detents on associated latch 410 may be releasably engaged with annular groove 401 disposed in second end 102 of biopsy needle 100b. For some applications, a plurality of tapered surfaces 403 may be formed on exterior portions of hub 140a proximate first end 142 to radially expand detent mechanisms associated with omega shaped latch 410 radially outward while inserting second end 102 of biopsy needle 100b into first end 251 of coupler assembly 250a. The detent mechanism may "snap" into annular groove 401 when aligned therewith. In a similar manner, a plurality of tapered surfaces 228 may be formed on exterior portions of end 224 of drive shaft 222 extending from powered driver 200 to radially expand detent mechanisms 421 and 422 radially outward during the insertion of end 224 of powered driver 200 into second end 252 of coupler assembly 250a. Detent mechanisms 421 and 422 will "snap" into annular groove 402 when aligned therewith.

Engagement between detent mechanisms associated with latch 410 with annular groove 401 of hub assembly 130a will generally retain second end 102 of biopsy needle 100b securely engaged with first end 251 of coupler assembly 250a. This engagement may allow powered driver 200 to rotate or spin cannula or biopsy needle 110b while withdrawing cannula or biopsy needle 110b from an insertion site. In a similar manner, engagement between detent mechanisms 421 and 422 of omega shaped latch 420 and annular groove 402 of end 224 of powered driver 200 will generally retain second end 252 of coupler assembly 250a engaged with powered driver 100 during withdrawal of cannula 110b from an insertion site.

Biopsy needle set 100b may be released from first end 251 of coupler assembly 250a by sliding first housing segment 280 longitudinally toward second end 262 of elongated core 260. Such movement of first housing segment 280 will result in interior tapered surface 286 contacting exterior portions of omega shaped latch 410 and compressing omega shaped latch 410 to radially expand associated detent mechanisms (not expressly shown) from engagement with annular groove 401 of hub assembly 130a. As a result, biopsy needle set 100b may be easily withdrawn from first end 251 of coupler assembly 250a. In a similar manner, longitudinal movement of second housing segment 290 toward first end 251 of coupler assembly 250a will result in interior tapered surface 296 contacting exterior portions of omega shaped latch 420 to compress generally omega shaped latch 420 and withdraw or retract detent mechanisms 421 and 422 from engagement with annular groove 402 of end 224. As a result, powered driver 200 and second end 222 of coupler assembly 250a may be easily disconnected from each other.

Flange 254 may be generally described as having an enlarged funnel shaped or bell shaped configuration. The dimensions and configuration of flange 254 may be selected to be compatible with end 211 of powered driver 200. As previously noted, coupler assembly 250a may be securely engaged with an opening formed in a containment bag or sterile sleeve in accordance with teachings of the present disclosure. For embodiments such as the one shown, end 272 of housing 270 of coupler assembly 250a may include annular ring 370 operable to be securely engaged with adjacent portions of flange 254. The outside diameter of annular ring 370 may generally correspond with the outside diameter of adjacent portions of flange 254. The inside diameter of annular ring 370 may also generally correspond with the inside diameter of adjacent portions of flange 254. For some embodiments a plurality of posts 372 and generally V shaped grooves 374 may be alternatingly disposed on the extreme end of flange 254. Annular ring 370 may include a plurality of holes 371 sized to received respective posts 372 therein. Annular ring 370 may also include a plurality of generally V shaped projections 376 sized to be received within respective generally V shaped grooves 374 formed in adjacent portions of flange 254. For embodiments such as the one shown, portions of a containment bag (e.g., around an opening) may be disposed between annular ring 370 and adjacent portions of flange 254. For example, post 372 may be inserted through a corresponding hole in a containment bag adjacent to the perimeter of an opening in the containment bag. Holes 371 in annular ring 370 may be aligned with respective posts 372. Other portions of a containment bag (e.g., adjacent to an opening) may be trapped between respective V shaped projections 376 and V shaped grooves 374. Various welding techniques including, but not limited to, laser welding may be applied to posts 372 to bond annular ring 370 with adjacent portions of flange 354. As a result, a perimeter of a containment bag around an opening in the containment bag may be securely engaged with second end 252 of coupler assembly 250a.

Figure 7A:
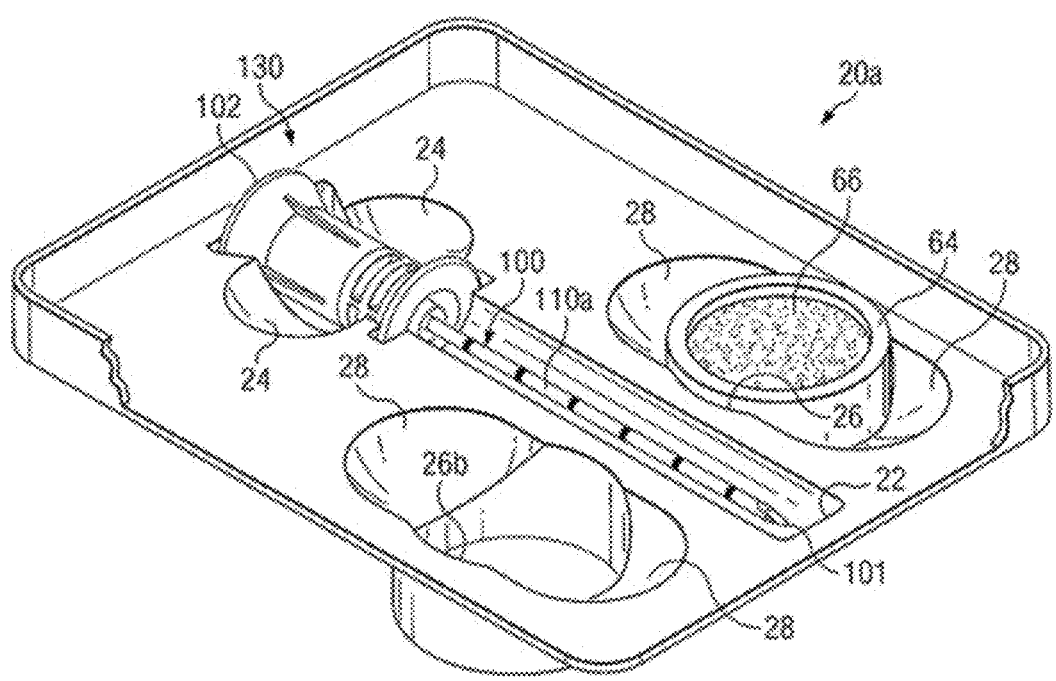
FIGS. 7A-7C depict various views of prior art kits.
Figure 7B:
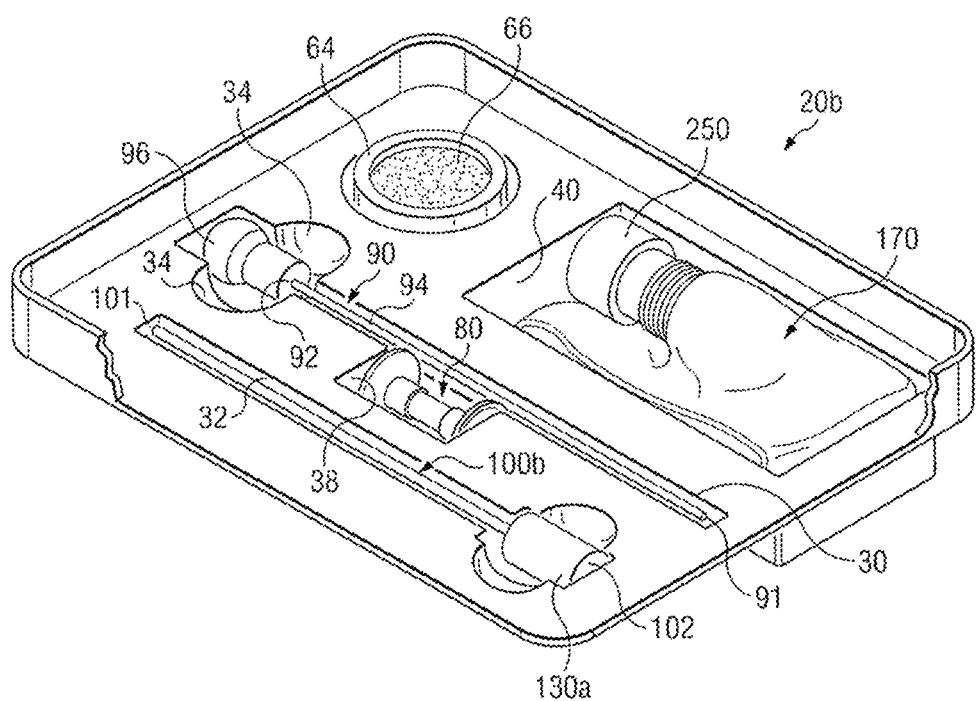
Figure 7C:
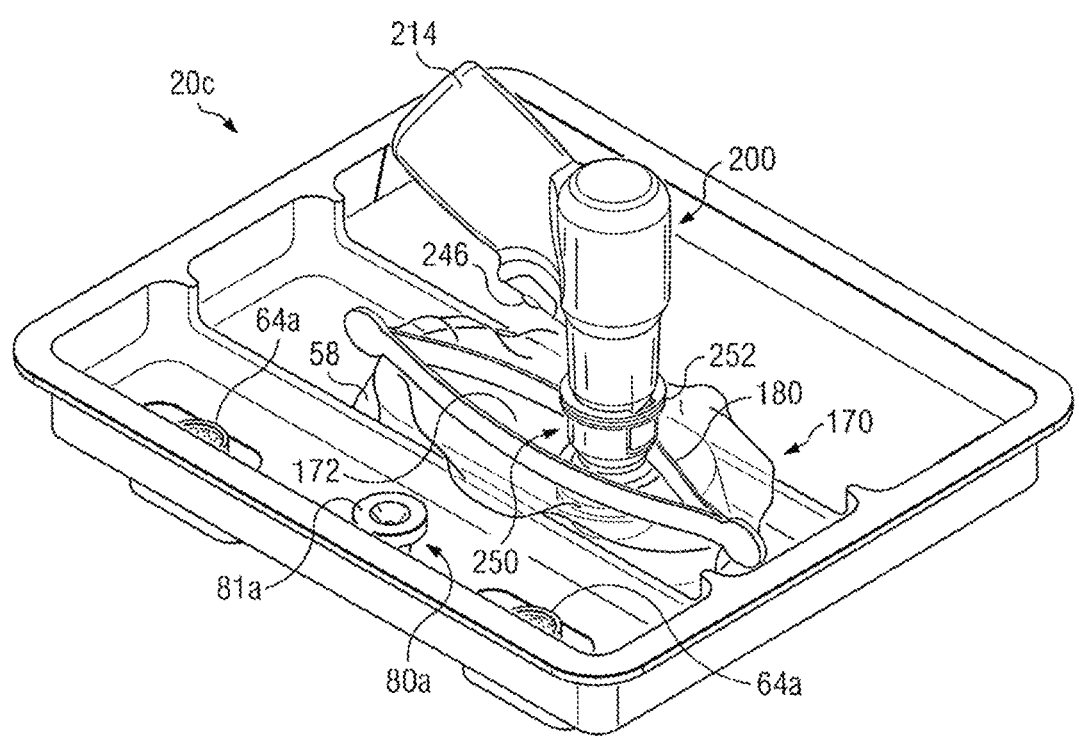

FIGS. 7A-7C show some examples of medical procedure trays and/or kits which may contain one or more intraosseous devices and/or other components incorporating teachings of the present disclosure. For example, medical procedure tray 20a as shown in FIG. 7A may include intraosseous needle set or aspiration needle set 100 incorporating various teachings of the present disclosure. Medical procedure tray 20b as shown in FIG. 7B may include intraosseous needle set or biopsy needle set 100b, ejector 90, funnel 80 and/or containment bag or sterile sleeve 170. Medical procedure tray 20c as shown in FIG. 7C may also include various IO devices and other components incorporating teachings of the present disclosure including, but not limited to, biopsy needle set 100b, coupler assembly 250, containment bag 170, ejector 90 and/or funnel 80a.

Medical procedure trays and/or kits formed in accordance with teachings of the present disclosure may provide a support or base for various components such as a coupler assembly, funnel, and/or sharps protector to allow an operator or user to perform various functions without requiring that the operator or user hold or manipulate the respective component. For example, medical procedure tray 20c as shown in FIG. 7C may position and support coupler assembly 250 such that one end of a powered driver may be inserted (pushed) into releasable engagement with second end 252 of coupler assembly 250. The powered driver may then be used to withdraw coupler assembly 250 from medical procedure tray 20c without requiring an operator or user to directly hold or manipulate coupler assembly 250.

Medical procedure trays 20a, 20b and/or 20c may also contain a wide variety of other components including, but not limited to, one or more sharps protectors 64 as shown in FIGS. 7A and 7B. Sharps protectors 64 may include hard foam or claylike material 66 disposed therein. Intraosseous devices such as aspiration needle sets and biopsy needle sets typically have respective sharp tips and/or cutting surfaces operable to penetrate skin, soft tissue and bone. The sharp tips and/or cutting surfaces of such intraosseous devices may be inserted into hard foam or claylike material 66 after completion of a medical procedure using the respective intraosseous device.

FIG. 7C shows one procedure for placing a powered driver within a containment bag incorporating teachings of the present disclosure. Containment bag 170 may be formed from generally flexible, fluid impervious material which may also be sterilized using conventional sterilization techniques. Containment bag 170 may be used to prevent a non-sterile powered driver from contaminating a sterile intraosseous device and/or an injection site, particularly during a bone marrow biopsy procedure or a bone marrow aspiration procedure. Containment bag 170 may be operable to form a fluid barrier with adjacent portions of housing assembly 270. At the same time, coupler assembly 250 may allow powered driver to rotate an intraosseous device releasably engaged with first end 251 of coupler assembly 250 without damage to containment bag 170.

Figure 8A:
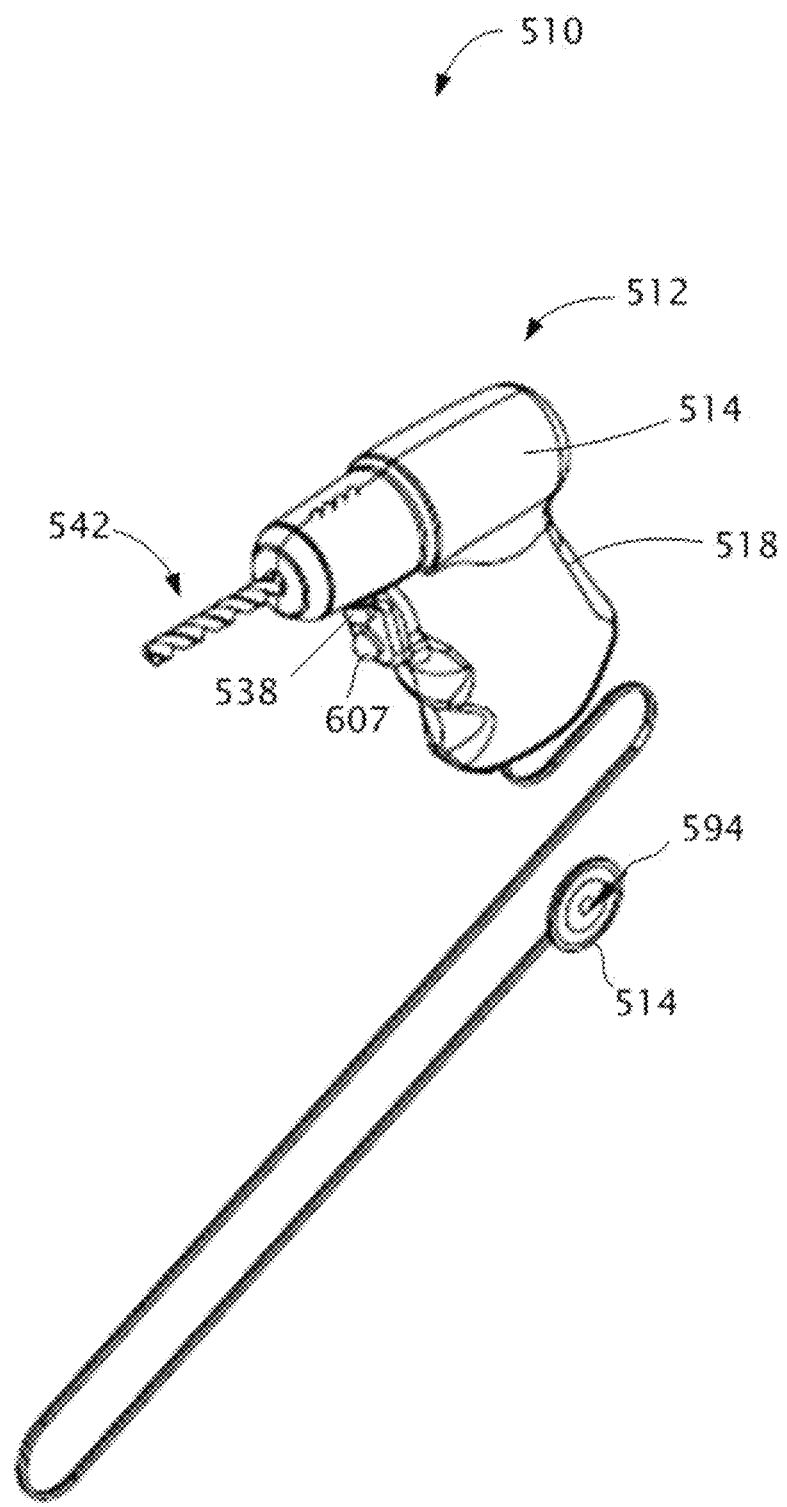
FIG. 8A depicts a perspective view of one embodiment of the present driver assemblies that has a driver with a sensor and a drill bit coupled to the driver, the driver assembly being configured to determine information about a target area, such as a location within biological material.
Figure 8B:
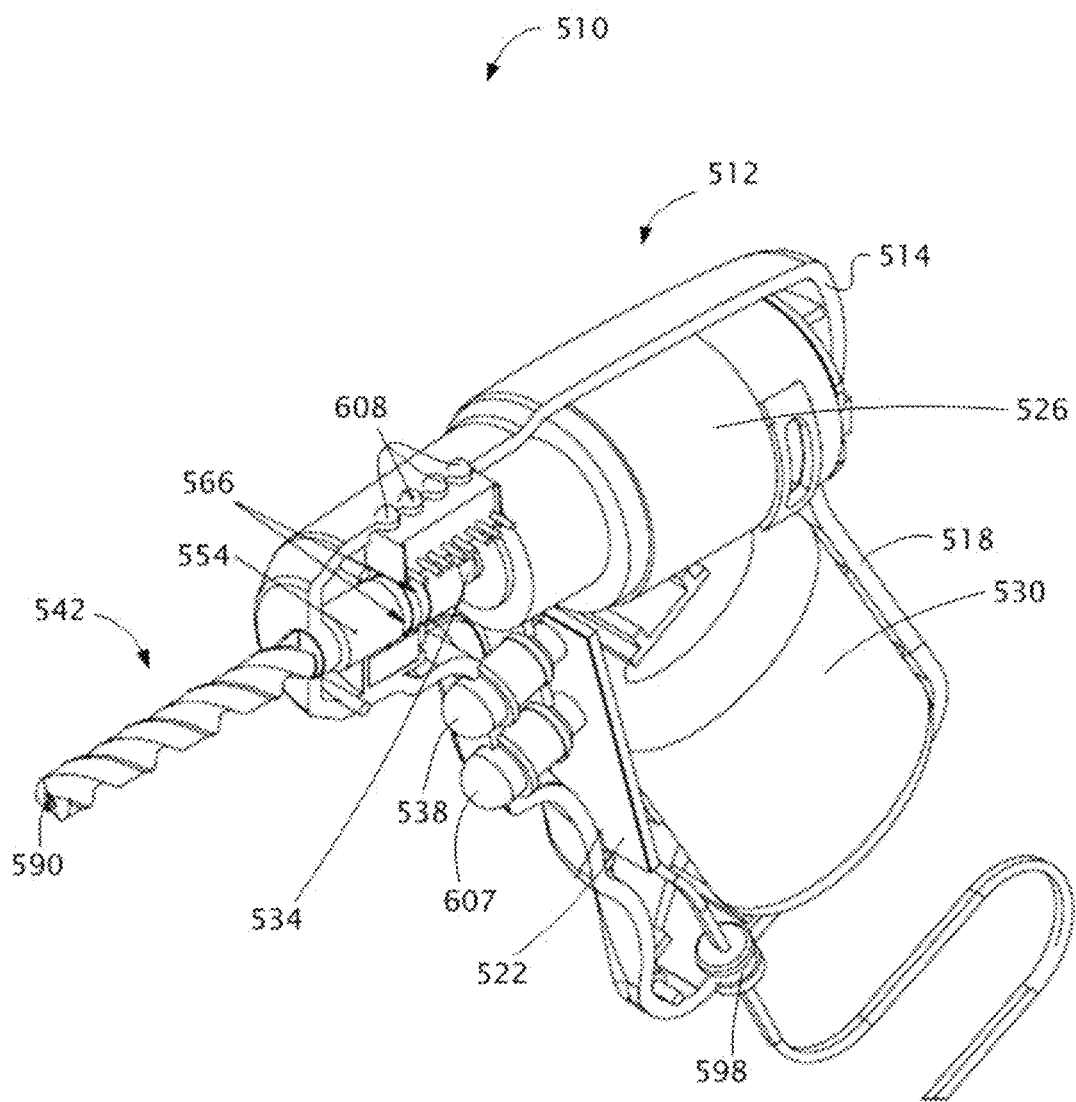
FIG. 8B depicts a portion of the interior of the driver of the driver assembly of FIG. 8A.

Referring now to FIGS. 8A-8B, designated by the reference numeral 510 is one embodiment of the present driver assemblies. Driver assembly 510 comprises driver 512 configured, for example, to rotate and/or move intraosseous needle sets and/or drill bits to penetrate a target area. Driver assembly 510 is configured to determine (and driver 512 is configured for use in determining), for example, a voltage and/or a voltage difference between a target area and another (e.g., non-target) area, an impedance at a target area, and/or determining a change in at least one of a voltage difference and/or an impedance. Embodiments of driver assembly 510 can comprise—but are not required to comprise—one or more components and/or characteristics of any of the other drivers and intraosseous devices described and depicted throughout this disclosure (e.g., FIG. 2).

In the embodiment shown, driver 512 comprises housing 514, which has a configuration similar to a pistol (e.g., having a barrel-shape, a handle, etc.). Various components associated with driver assembly 510, and more specifically with driver 512, are disposed within housing 514. Housing 514 may comprise substantially rigid polymeric material (e.g., a polycarbonate) and, in some embodiments, housing 514 can comprise a single piece of material; in other embodiments, housing 514 can comprise more than one piece of material (e.g., two halves coupled with a fluid tight seal). In the embodiment shown, housing 514 includes handle 518, which can have various configurations, including, for example, being configured to be gripped by a user.

In the embodiment shown, driver 510, and more specifically driver 512, includes controller 522. Controller 522 can be configured to control various components (e.g., a motor) of driver 512. Controller 522 can also be configured to determine various characteristics (e.g., voltage, voltage differences, impedances, changes in at least one of voltage differences and impedances, and the like) of a target and/or another (e.g., a non-target) area. In the embodiment shown, driver 512 also includes motor 526 coupled to power source 530 (e.g., a battery) and further coupled to controller 522. Controller 522 can be configured, for example, to activate and/or deactivate motor 526 (based on, for example, user input, position of an intraosseous device (such as a drill bit) within a target area, an impedance, a voltage difference, or a change in at least one of an impedance and a voltage difference).

In the embodiment shown, driver 512 also includes drive shaft 534 coupled to motor 526 such that motor 526 can rotate drive shaft 534. Drive shaft 534 can be configured similarly to other embodiments of drive shafts described and depicted throughout this disclosure (e.g., FIG. 2). In some embodiments, drive shaft 534 can be coupled to motor 526 by a gear assembly (e.g., gear assembly 220, in previously described embodiments). In some embodiments, drive shaft 534 can have a substantially hexagonal cross-section (e.g., corresponding to the coupler assembly depicted in FIG. 6C). In other embodiments, drive shaft 534 can have a cross-section with any shape configured to be coupled to a corresponding intraosseous device, such as a drill bit or a needle set.

In the embodiment shown, driver 512 includes trigger 538, which can be coupled to motor 526 and/or controller 522. Trigger 538 can be engaged to activate (and/or deactivate, in some embodiments) motor 526 to permit motor 526 to rotate drive shaft 534 and any coupled intraosseous device.

Figure 8C:
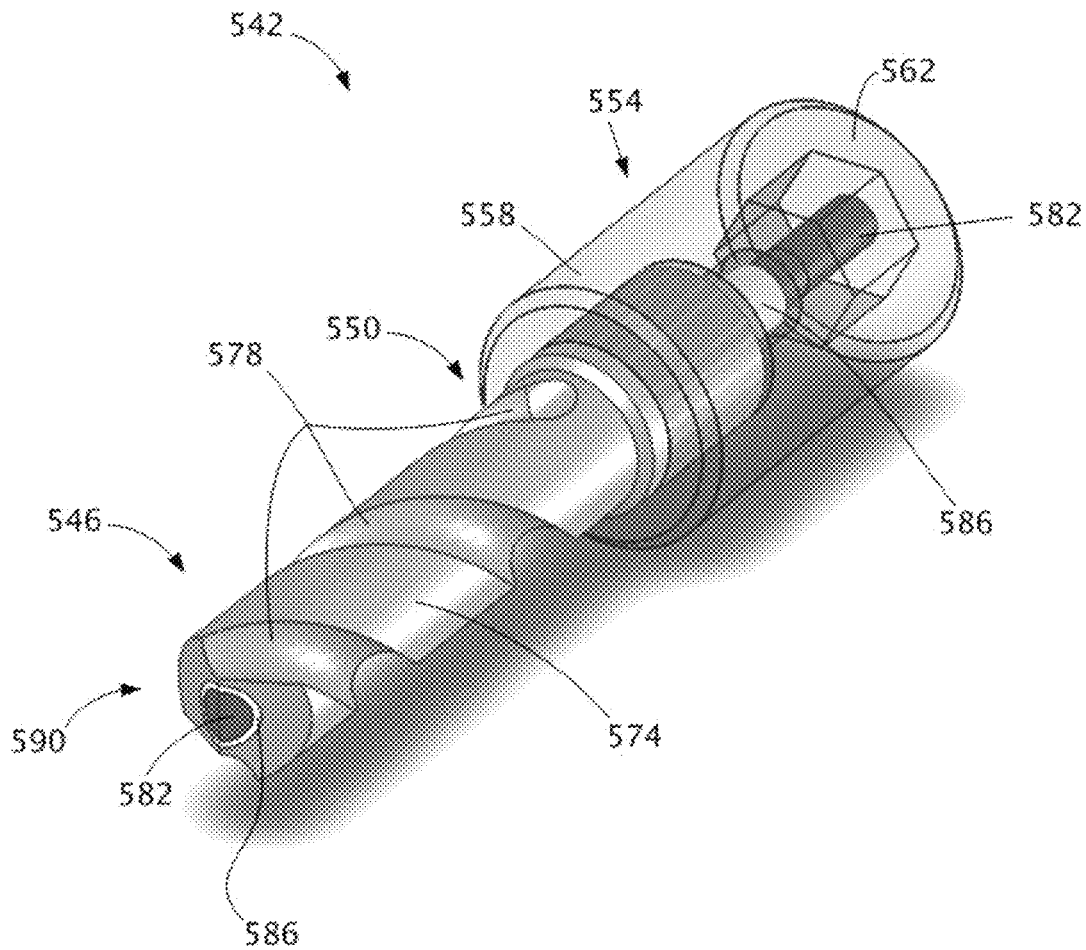
FIG. 8C depicts an enlarged view of one embodiment of the present drill bits, which embodiment is shown in FIGS. 8A and 8B.

In the embodiment shown, driver assembly 510 also includes drill bit 542 (FIG. 8C), which is configured to be coupled to driver 512. In this disclosure, a first structure that is configured to be coupled to a second structure can be not coupled to the second structure or it can be coupled to the second structure (and, in either case, is still configured to be coupled to the second structure). Drill bit 542 includes an exposed portion (an exposed distal portion, in this embodiment) having a first end 546 and second end 550. Drill bit 542 can be—but is not required to be—coupled to drive shaft 534 similarly to the ways in which other intraosseous devices (e.g., needle sets) discussed throughout this disclosure can be coupled to a drive shaft (e.g., via a coupler assembly having a hub). In the embodiment shown, for example, driver assembly 510 comprises drill bit coupler 554, which can be part of drill bit 542 when an operator first obtains the drill bit for use, or which can be an element separate from and couplable to drill bit 542 when an operator first obtains the drill bit for use (such as either being a structure that can be coupled to driver 512 or that is coupled to driver 512 when an operator first obtains the driver for use). Drill bit coupler 554 includes first end 558 configured to be coupled (e.g., detachably) to second end 550 of drill bit 542. Drill bit coupler 554 also includes second end 562 configured to be coupled (e.g., detachably) to drive shaft 534 (e.g., by a female hexagonal configuration corresponding to a male hexagonal configuration of drive shaft 534). Drill bit coupler 554 can be insulated (such as, for example, by comprising an insulator (e.g., polytetrafluoroethylene)) to substantially prevent heat and/or electricity from drill bit 542 from passing beyond drill bit coupler 554.

In the embodiment shown, second end 550 of drill bit 542 is further configured to be coupled to controller 522 by a commutating electrical connection (e.g., via a gear box bearing) to permit electrical communication between drill bit 542 and controller 522. For example, in the embodiment shown, driver 512 has at least one drill bit contact 566 coupled (e.g., slidably) to drill bit 542 and to controller 522. Drill bit contact 566 is configured to provide a commutating electrical connection between drill bit 542 and controller 522. Drill bit contact 566 can comprise a non-conductive coating (e.g., a dielectric, such as polytetrafluoroethylene) configured to substantially prevent electricity from drill bit 542 from passing beyond drill bit contact 566.

In the embodiment shown, drill bit 542 is configured to penetrate a target area (e.g., target area 570). Drill bit 542 includes outer surface 574 extending from second end 550 to first end 546 of the exposed portion of drill bit 542. Outer surface 574 has groove(s) 578 (e.g., thread(s)) that help enable drill bit 542 to penetrate biological material (e.g., bone) to reach a target area (e.g., an IO space within bone or cerebrospinal fluid within a subject's skull). In the embodiment shown, drill bit 542 also includes core 582 extending the length (also characterizable as the entire length) of drill bit 542, from first end 546, beyond second end 550, and to the proximal end of the drill bit. In other embodiments, however, core 582 can extend less than the length of drill bit 542 (e.g., and be exposed to biological material at points along drill bit 542 other than at a tip of drill bit 542). Core 582 can be disposed inside at least outer surface 574. In the embodiment shown, drill bit 542 also includes insulator 586 (e.g., comprising a non-conductive material, such as polytetrafluoroethylene) extending from a location distal of the proximal end of the drill bit (and thus distal of the proximal end of core 582), past second end 550, to first end 546 of drill bit 542. Insulator 586 can be disposed at least between core 582 and outer surface 574 to prevent electrical communication between core 582 and outer surface 574. In some embodiments, insulator 586 has a thickness of 0.001 millimeters to 2 millimeters. In other embodiments, insulator 586 can have a thickness of less than 0.001 millimeters or more than 2 millimeters (e.g., depending on electricity flowing through core 582).

In the embodiment shown, outer surface 574, core 582, and insulator 586 can be configured to cooperate to form at least one tip 590 at first end 546 of drill bit 542. Tip 590 can be configured to penetrate a target area (e.g., target area 570) in various ways (e.g., similarly to other intraosseous devices described and depicted throughout this disclosure (e.g., by having one or more cutting surfaces)). In the embodiment shown, a portion of core 582 is exposed at tip 590 to permit electrical communication between tip 590 and a target area. In the embodiment shown, drill bit contact 566 is configured to permit electrical communication between controller 522 and at least one of core 582 and outer surface 574. For example, controller 522 can be configured to determine (e.g., through drill bit contact 566) at least one of current, voltage, impedance, and temperature from outer surface 574 and/or core 582.

Figure 8D:
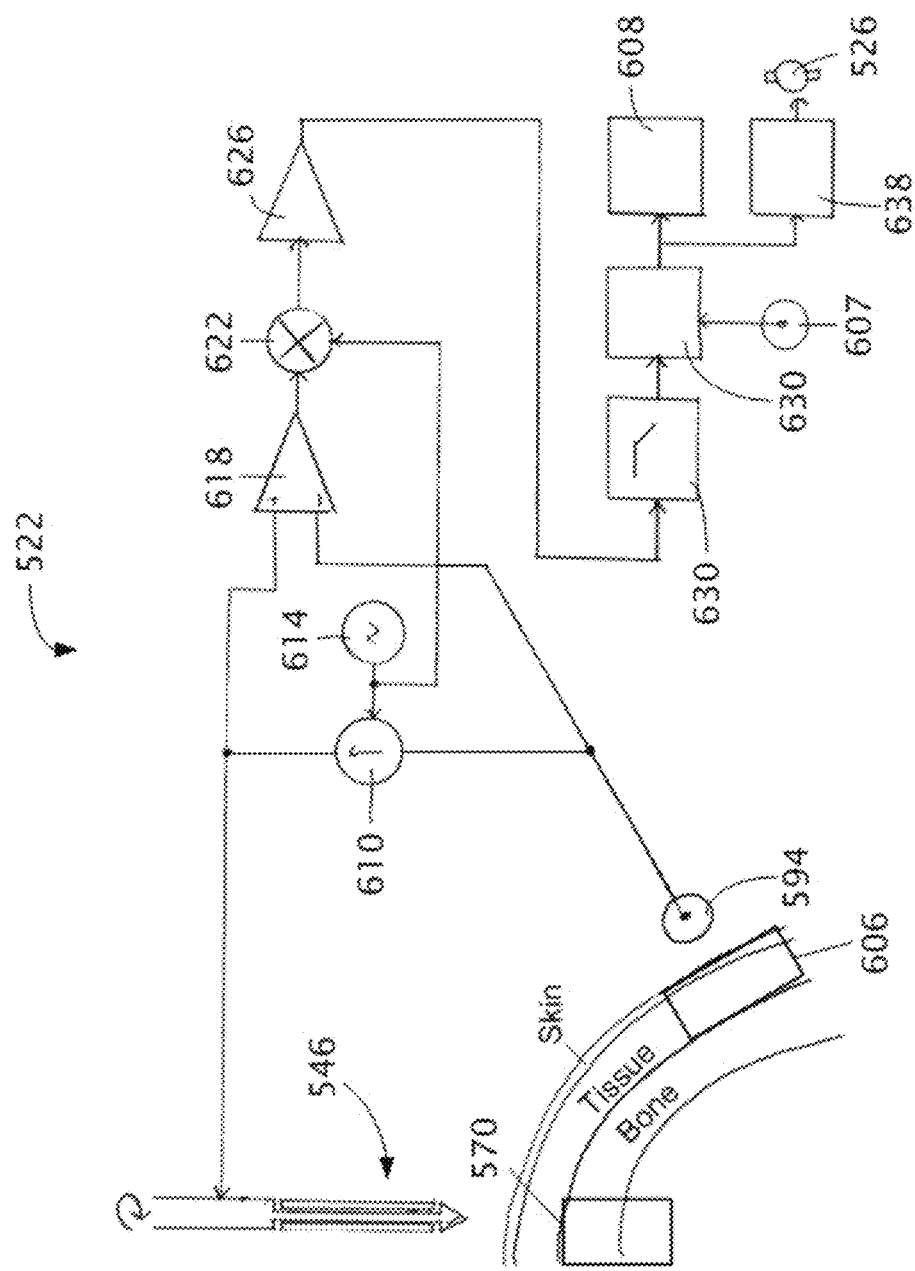
FIG. 8D depicts one embodiment of a circuit diagram for a controller of the driver assembly (and, more specifically, of the driver) of FIG. 8A.

In the embodiment shown (e.g., depicted in FIGS. 8A, 8D, and 8E), driver assembly 510 (and, more specifically, driver 512) also includes at least one first electrode 594 (e.g., forming a two-wire configuration with controller 522 as depicted in FIG. 8D). First electrode 594 can be placed (e.g., using an adhesive) in or on a non-target area (e.g., non-target area 598 comprising biological material, such as skin and/or tissue surrounding bone). Such non-target area may also be near (e.g., in proximity to) a target area (e.g., target area 570 comprising biological material, such as bone and/or bone marrow in the embodiment shown). In some embodiments, the closer the non-target area is to the target area, the more effective the driver assembly (and, more specifically, the driver) will be in determining the desired information (e.g., a voltage difference between core 582 and first electrode 594, an impedance of biological material between core 582 and first electrode 594, a change in the voltage difference between core 582 and first electrode 594, and/or a change in the impedance of the biological material between core 852 and first electrode 594). In other embodiments, the driver assembly (and, more specifically, the driver) will be more effective in determining the desired information where the non-target area is farther from the target area (e.g., to minimize voltage gradients at a target area caused by or resulting from first electrode 594). As those of ordinary skill in the art will understand, the anatomy of interest for a procedure will impact the location or position of first electrode 594 with respect to a target area (e.g., one skilled in the art may avoid positioning time varying impedance artifacts (e.g., cardiac activity, respiration, etc.) between core 582 and first electrode 594). First electrode 594 is configured to be coupled to controller 522, for example, by patch connector 598. In the embodiment shown, first electrode 594 is coupled (e.g., by a floating connection) to an inverting input of a differential amplifier (e.g., and thus coupled to controller 522). Controller 522 can be configured to determine a voltage difference and/or an impedance between core 582 and first electrode 594. Controller 522 can further be configured to determine a change in a voltage difference and/or a change in impedance (e.g., based on a previous voltage difference and/or impedance, a reference voltage difference and/or reference impedance, and the like). In some embodiments, an impedance and/or a voltage difference between core 582 and first electrode 594 can be substantially similar to an impedance and/or a voltage difference, respectively, at a target area (depending, for example, on the location of the target area and the position of core 582). Various other configurations can be used to determine information about a target area, such as, for example, using a drill bit comprising a split ring electrode core, a three-wire configuration, a four-wire configuration, and the like.

Figure 8E:
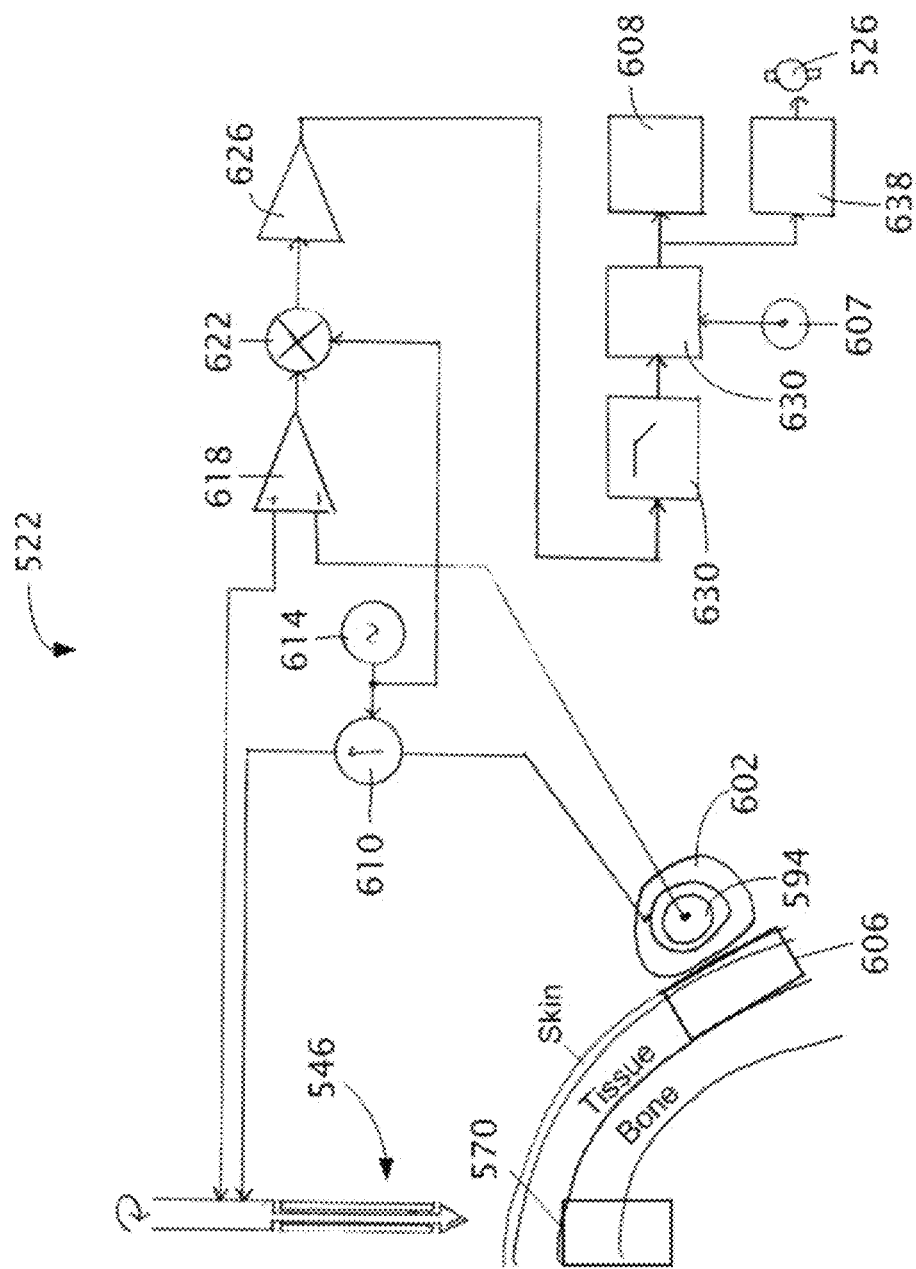
FIG. 8E depicts another embodiment of a circuit diagram for a controller of the driver assembly (and, more specifically, of the driver) of FIG. 8A.

In the embodiment shown, driver assembly 510 can further comprise at least one second electrode 602 coupled to controller 522, such as by patch connector 598 (e.g., forming at least a three-wire configuration as depicted in FIG. 8E). In the embodiment shown, second electrode 602 can be placed (e.g., using an adhesive) in or on a non-target area (e.g., non-target area 606). Second electrode 602 can be placed in various positions with respect to first electrode 594 and a non-target area, such as, for example, concentric with first electrode 594 (e.g., such that second electrode 602 encircles first electrode 594). In other embodiments, however, second electrode 602 can comprise various other shapes (e.g., rectangular) and can be placed in various other positions with respect to first electrode 594 (e.g., parallel to first electrode 594). In the embodiment shown, controller 522 can be configured to pass a current (e.g., an alternating current (e.g., at 50 KHz)) to second electrode 602, meaning the controller is involved in (or plays a role in) causing a current to pass to the second electrode. In some embodiments, controller 522 can be configured to pass the same current to core 582 and second electrode 602. For example, controller 522 can pass a current to second electrode 602 having a frequency of 5 kHz to 150 kHz. In the embodiment shown, second electrode 602 is involved in (or plays a role in) permitting controller 522 to determine, for example, a voltage difference between first electrode 594 and core 582, a change in such a voltage difference, an impedance in proximity to (or near) drill bit 542 and/or a target area (e.g., target area 570), and a change in such an impedance. For example, second electrode 602 can assist in decreasing or minimizing interference (e.g., near field effects) from a non-target area when determining information (e.g., a voltage difference, a change in voltage difference, an impedance, and/or a change in impedance) related to a target area. As those of ordinary skill in the art will understand, the anatomy of interest for a procedure will impact the location or position of first electrode 594 and/or second electrode 602 relative to the location or position of a target area and/or a non-target area.

Controller 522 can be configured to determine information about a target area (e.g., a target area in biological material) in a variety of ways. In the embodiment shown, controller 522 is configured to determine a change in an impedance and/or a change in a voltage difference (e.g., between a target area and a non-target area) by, at least in part, reference to a point within the target area, an impedance, and/or a voltage difference. For example, driver 510 comprises reference button 607 coupled to controller 522. Reference button 607 is configured to set (e.g., when a user engages reference button 607) a reference point (e.g., marking a physical position within a target area), a reference impedance (e.g., marking an impedance at a point within a target area), and/or a reference voltage difference (e.g., marking a voltage difference (e.g., between a target area and a non-target area) at a point within a target area). In other embodiments, controller 522 can be configured to set a reference point, a reference impedance, and/or a reference voltage difference automatically when drill bit 542 contacts a predetermined point (e.g., a bone). If a reference point, a reference impedance, and/or a reference voltage difference is set (e.g., by a user engaging reference button 607, automatically, etc.), controller 522 is configured to determine a change from the reference point, reference impedance, and/or reference voltage difference, respectively. Controller 522 can be configured to determine a change in impedance and/or a change in voltage difference by determining an impedance and/or voltage difference greater or less than the reference impedance and/or the reference voltage difference, respectively. In other embodiments, for example, controller 522 can be configured to determine a first impedance (e.g., an impedance of bone) and/or a first voltage difference (e.g., between a target and a non-target area) at a first depth within the target area and also determine a second impedance (e.g., an impedance of bone marrow) and/or a second voltage difference at a second depth within the target area. Controller 522 can also be configured to determine a change in impedance and/or a change in voltage difference between the first impedance and/or the first voltage difference and the second impedance and/or the second voltage difference, respectively. In other embodiments, controller 522 can be configured to determine a plurality (e.g., two or more) of impedances and/or voltage differences corresponding to a plurality of depths within a target area. Controller 522 can then be configured to determine a change in impedance and/or a change in voltage difference between the plurality of impedances and/or voltage differences, respectively.

In the embodiment shown, controller 522 can be configured to display information relating to a target area to a user. Driver assembly 510 (and, more specifically, driver 512) can comprise display 608 (e.g., one or more light emitting diodes, a liquid crystal display, and/or noise indicators) configured to be coupled to controller 522 and configured to display information relating to at least one of an impedance, a change in an impedance, a voltage difference, and/or a change in a voltage difference. In the embodiment shown, display 608 comprises a plurality of light emitting diodes. In some embodiments, display 608 can be configured to display additional information, such as, for example, a position of a drill bit within a target area, or a depth of a drill bit within a target area (e.g., based on an impedance, a change in an impedance, a voltage difference, and/or a change in a voltage difference).

In the embodiment shown, controller 522 includes various components configured to permit controller 522 to determine information relating to a target area, display such information, and control a motor. For example, in the embodiment shown, controller 522 comprises current source 610 configured to produce a current to pass to second electrode 602 and core 582 of drill bit 542. In the embodiment shown, current source 610 is configured to produce and/or pass a current (e.g., 100 uA to 10 mA) having a frequency of 5 kHz to 150 kHz. In other embodiments, current source 610 can be configured to produce and/or pass a current having a frequency of less than 5 kHz and greater than 150 kHz (depending, for example, on a location of a given target area, resistance in controller 522, resistance in core 582, and resistance in second electrode 602).

In the embodiment shown, controller 522 also includes oscillator 614 configured to produce a signal in the current produced by current source 610, such as, for example, an alternating current. For example, in the embodiment shown, oscillator 614 can produce a signal having a frequency of 5 kHz to 150 kHz. In other embodiments, oscillator 614 can be configured to produce a signal having a frequency of less than 10 kHz and greater than 100 kHz (depending, for example, on a location of a given target area, resistance in controller 522, resistance in core 582, and resistance in first electrode 594).

In the embodiment shown, controller 522 also includes differential amplifier 618, which can be, for example, a high common mode rejection differential input amplifier. Differential amplifier 618 can be coupled to (e.g., electrically) and configured to receive a voltage from core 582 of drill bit 542. Differential amplifier 618 can also be coupled to (e.g., electrically) and configured to receive a voltage from first electrode 594. In the embodiment shown, differential amplifier 618 is configured to output a voltage difference between core 582 and first electrode 594 while a current is applied to second electrode 602 and core 582. The output from differential amplifier 618 is a function of and/or correspond to, for example, an impedance at (or near) a target area (e.g., biological material in proximity to (or near) drill bit 542). Core 582 and first electrode 594 can be coupled to the inputs of differential amplifier 618 in any configuration (e.g., based on a desired signal phase for the output).

In the embodiment shown, controller 522 also includes multiplier 622, which can be coupled (e.g., electrically) to oscillator 614 and differential amplifier 618. In the embodiment shown, multiplier 622 is configured to multiply a signal from differential amplifier 618 with a signal from oscillator 614 to down convert the voltage output from differential amplifier 618 to produce a baseband frequency (e.g., similarly to a lock-in amplifier). In the embodiment shown, multiplier 618 can produce a direct voltage as a function of and/or that corresponds to an impedance at (or near) a target area.

In the embodiment shown, controller 522 also comprises gain amplifier 626, which can be coupled (e.g., electrically) to multiplier 618. In the embodiment shown, gain amplifier 626 is configured to increase a voltage of a baseband frequency produced by multiplier 622. For example, gain amplifier 626 can increase the voltage by a factor of 1000. In other embodiments, gain amplifier 626 can increase the voltage by a factor of 100 to 10,000 depending, for example, on a location of a given target area and/or resistance in controller 522. A required system gain can be, for example, optionally distributed between differential amplifier 618 and gain amplifier 626.

In the embodiment shown, controller 522 also includes low pass filter 630, which can be coupled (e.g., electrically) to gain amplifier 626. Low pass filter 630 is configured to receive a signal from gain amplifier 626 and attenuate a signal having a higher frequency than a predetermined cutoff frequency.

In the embodiment shown, driver assembly 510 (and, more specifically, driver 512) is configured such that display 608 notifies a user if a change in an impedance and/or a change in a voltage difference meets or exceeds a threshold (e.g., a predetermined threshold, which can be positive or negative, and the exceeding of a negative threshold can be a negative value that is more negative than the negative threshold). Controller 522 includes threshold detector 634 coupled (e.g., electrically) to low pass filter 630. Threshold detector 634 has a predetermined threshold (such as, for example, one that corresponds to a voltage difference, an impedance, or a current). In some embodiments, the predetermined threshold is adjustable, such that a user can set the threshold. In other embodiments, driver assembly 510 can permit a user to select from pre-programmed thresholds that, for example, correspond to various target areas (e.g., cranium, sternum, and the like). Low pass filter 630 can output a signal, and if the signal meets or exceeds a predetermined threshold of threshold detector 634, controller 522 can cause display 608 to indicate, for example, at least one of an impedance, a change in an impedance, a voltage difference, a change in a voltage difference, a position of drill bit 542 within a target area, and any other relevant information related to impedance, voltage, and/or location of drill bit 542 within a target area.

In the embodiment shown, driver assembly 510 (and, more specifically, driver 512) also includes motor controller 638. Controller 522 is configured to permit motor controller 638 to deactivate (and/or activate, in some embodiments) motor 526 if a change in an impedance and/or a change in a voltage difference meets or exceeds a predetermined threshold. In other embodiments, controller 522 can be configured to permit motor controller 638 to change (e.g., increase and/or decrease) a rotational speed of motor 526 (e.g., and indirectly drill bit 542) if a change in an impedance and/or a change in a voltage difference meets or exceeds a predetermined threshold.

The present drill bits, drivers, and driver assemblies may be used, for example, in any procedure in which it is desirable to identify (whether automatically or through a notification that can be recognized by a user) a change in the biological material through which an IO device (such as a drill bit or a needle set) is advancing. A craniotomy is one example of such a procedure. Another example is the placement of a needle set in an IO space within the sternum. Some embodiments of the present methods of determining an impedance, a change in an impedance, a voltage difference, and/or a change in a voltage difference relating to a target area and/or a non-target area with an embodiment of the present driver assemblies comprise placing a first electrode (e.g., first electrode 594) of a driver assembly (e.g., driver assembly 510) in or on a non-target area (e.g., non-target area 606), moving a drill bit (e.g., drill bit 542) of the driver assembly through biological material (e.g., skin and tissue) toward a target area (e.g., target area 570, such as bone marrow or a location inside the skull (such as a location occupied by cerebrospinal fluid)) in biological material, and determining at least one of an impedance (e.g., at or near a target area), a change in an impedance, a voltage difference (e.g., between a target area and a non-target area), and a change in a voltage difference. In some embodiments, the method can further comprise placing a second electrode (e.g., second electrode 602) in or on the non-target area (e.g., forming at least a three-wire configuration to minimize or decrease near field effects of a non-target area). Further, the method can comprise displaying a notification when at least one of the impedance, the change in an impedance, the voltage difference, and/or the change in a voltage difference meets or exceeds a threshold. As another example, the method can comprise changing and/or stopping a rotational velocity of the drill bit when at least one of the impedance, the change in an impedance, the voltage difference, and/or the change in a voltage difference meets or exceeds a threshold. The method can further comprise removing the drill bit from the target area, such as to permit access to the target area.

A method of determining an impedance, a change in an impedance, a voltage difference, and/or a change in a voltage difference with an embodiment of the present driver assemblies can comprise, for example, placing a first electrode (e.g., first electrode 594) of a driver assembly (e.g., driver assembly 510) in or on a non-target area (e.g., non-target area 606), moving a drill bit (e.g., drill bit 542) of the driver assembly through biological material toward a target area (e.g., target area 570) in biological material, setting at least one of a reference impedance and a reference voltage difference, and determining a change from at least one of the reference impedance and the reference voltage difference such as in a manner described above. In some embodiments, the method can further comprise placing a second electrode (e.g., second electrode 602) in or on the non-target area (e.g., to form at least a three-wire configuration to minimize or decrease near field effects of a non-target area). Further, the method can comprise displaying a notification when at least one of the impedance, the change in an impedance, the voltage difference, and/or the change in a voltage difference meets or exceeds a threshold. As another example, the method can comprise changing and/or stopping a rotational velocity of the drill bit when at least one of the impedance, the change in an impedance, the voltage difference, and/or the change in a voltage difference meets or exceeds a threshold. The method can also comprise removing the drill bit from the target area, such as to permit access to the target area.

Similarly to other embodiments of intraosseous devices (or components of intraosseous devices) described in this disclosure, embodiments of the present drivers, driver assemblies, and drill bits (and components of such embodiments) can also be included in one or more kits. A kit comprising one or more embodiments (or one or more components) of the present driver assemblies can comprise one or more IO devices (or one or more components of IO devices) of any of the kits described in this disclosure (e.g., as depicted in FIG. 7A-7C). For example, a kit can comprise a driver (e.g., driver 510) and an intraosseous device configured to be coupled to the driver (e.g., drill bit 542). In some embodiments, a kit can also comprise at least one of a cannula and a stylet. In some embodiments, a kit can further comprise a coupler configured to couple the driver to the intraosseous needle set. In other embodiments, the kit can comprise an aspiration device configured to be coupled to a cannula. In some embodiments, a kit can comprise at least one sharps protector configured such that at least one of the cannula, the stylet, and the drill bit can be disposed in the sharps protector to prevent exposure of a cutting surface. In other embodiments, a kit can comprise a containment assembly configured to seal the driver inside the containment assembly to prevent desterilization of at least one of the intraosseous needle set and a target area.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives falling within the scope of the claims, and embodiments other than the one shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A driver assembly comprising:
 a driver comprising:
  a motor configured rotate a drive shaft;
  a controller coupled to the motor and configured to control the motor; and
  a trigger coupled to the controller and configured to activate the motor;
 a first electrode coupled to the controller; a drill bit configured to be coupled to the drive shaft and the controller, the drill bit comprising:
  an outer surface having a first end and a second end;
  a core extending from the first end of the outer surface and beyond the second end of the outer surface, such that a first end of the core is disposed within the first end of the outer surface and a second end of the core extends beyond the second end of the outer surface; and
  an insulator disposed between the core and the outer surface configured to prevent electrical communication between the core and the outer surface;
 where the first end of the outer surface, the insulator, and the core cooperate to form at least one tip of the drill bit;
 where the second end of the outer surface is configured to be coupled to the drive shaft; and
 where the controller is configured to determine at least one of a voltage difference between the core and the first electrode and an impedance between the core and the first electrode when the driver assembly is used in a medical procedure.

2. The driver assembly of claim 1, further comprising:
 a second electrode configured to be coupled to the controller,
 where the controller is configured to pass a current to the second electrode and to the core of the drill bit when the second electrode and the drill bit are coupled to the controller,
 where the controller is configured to determine at least one of a voltage difference between the core and the second electrode and an impedance between the core and the second electrode when the controller passes the current to the second electrode and the core.

3. The driver assembly of claim 1, where the controller is configured to determine a change in at least one of the voltage difference and the impedance between the core and the first electrode when the drill bit moves through biological material.

4. The driver assembly of claim 3, where the controller deactivates the motor when the change in at least one of the voltage difference and the impedance between the core and the first electrode meets or exceeds a threshold value.

5. The driver assembly of claim 3, where the controller changes a rotational speed of the motor when the change in at least one of the voltage difference and the impedance between the core and the first electrode meets or exceeds a threshold value.

6. The driver assembly of claim 3, further comprising:
 a display coupled to the controller and configured to display information relating to at least one of: the voltage difference between the core and the first electrode, the impedance between the core and the first electrode, and the change in at least one of the voltage difference and the impedance between the core and the first electrode.

7. The driver assembly of claim 6, where the display is configured to indicate information about a position of the drill bit based on the voltage difference between the core and the first electrode, the impedance between the core and the first electrode, and the change in at least one of the voltage difference and the impedance between the core and the first electrode.

8. The driver assembly of claim 6, further comprising:
a reference button coupled to the controller, the reference button configured to set at least one of a reference voltage difference between the core and the first electrode and a reference impedance between the core and the first electrode, and the controller configured to determine a change from at least one of the reference voltage difference and the reference impedance between the core and the first electrode.

9. The driver assembly of claim 8, where the controller comprises a threshold detector configured to compare the change from at least one of the reference voltage difference and the reference impedance between the core and the first electrode to a threshold value.

10. A driver comprising:
a motor configured to rotate a drive shaft;
a controller coupled to the motor and configured to control the motor;
a trigger coupled to the controller and configured to activate the motor;
a coupler having a first end and a second end, the first end of the coupler configured to couple to an intraosseous (IO) device and the second end of the coupler configured to couple to the drive shaft;
where the coupler comprises an insulating material configured to prevent at least one of heat or electricity from passing beyond the coupler;
where the driver is coupled to a first electrode;
where the driver is configured to determine at least one of a voltage difference between the IO device and the first electrode and an impedance between the IO device and the first electrode when the coupler is coupled to the IO device and the drive shaft;
where the IO device comprises an outer surface having a first end and a second end, and a core extending from the first end of the outer surface and beyond the second end of the outer surface, such that a first end of the core is disposed within the first end of the outer surface and a second end of the core extends beyond the second end of the outer surface, and where the second end of the outer surface is configured to be coupled to the coupler; and
where the IO device is configured to penetrate a target area comprising biological material.

11. The driver of claim 10, further comprising:
a second electrode configured to be coupled to the controller;
where the controller is configured to pass a current to the second electrode and to the IO device when the second electrode and the IO device are coupled to the controller,
where the controller is configured to determine at least one of a voltage difference between the IO device and the second electrode and an impedance between the IO device and the second electrode when the controller passes the current to the second electrode and the IO device.

12. The driver of claim 11, where the controller is configured to determine at least one of a voltage difference, an impedance, a change in a voltage difference, and a change in an impedance when at least one of the first and second electrodes is coupled to the controller and the driver is used with the IO device to penetrate the target area.

13. The driver of claim 12, where the controller is configured to compare the at least one of the voltage difference, the impedance, the change in a voltage difference, and the change in an impedance to a threshold.

14. The driver of claim 10, further comprising:
a reference button coupled to the controller, the reference button configured to be engaged by a user,
where the controller is configured to determine at least one of a reference voltage difference and a reference impedance when the IO device is penetrated a first depth into the target area and the reference button is engaged;
where the controller is configured to determine at least one of a change in impedance from the reference impedance and a change in voltage difference from the reference voltage difference when the TO device is penetrated a second depth into the target area.

15. The driver of claim 14, where the controller is configured to compare at least one of the change in impedance from the reference impedance and the change in voltage difference from the reference voltage difference to a threshold value.

16. The driver of claim 15, where the threshold is adjustable.

17. A drill bit comprising:
an outer surface having a first end and a second end;
a core extending from the first end of the outer surface and beyond the second end of the outer surface, such that a first end of the core is disposed within the first end of the outer surface and a second end of the core extends beyond the second end of the outer surface; and
an insulator disposed between the core and the outer surface configured to prevent electrical communication between the core and the outer surface;
where the first end of the outer surface, the insulator, and the core cooperate to form at least one tip of the drill bit configured to penetrate bone;
where the second end of the outer surface is configured to be coupled to a drive shaft of a driver; and
where the drill bit is configured to be used to determine at least one of a voltage difference and an impedance across biological material during a medical procedure.

18. The drill bit of claim 17, where the drill bit is configured to be coupled to the drive shaft of the driver by a commutating electrical connection.

19. The drill bit of claim 18, where the drill bit is configured to be coupled to the drive shaft by a drill bit contact, the drill bit contact configured to permit a commutating electrical connection between the drill bit and the drive shaft of the driver.

20. The driver assembly of claim 1, where the outer surface of the drill bit comprises a rounded groove.

* * * * *